(12) United States Patent
Preville et al.

(10) Patent No.: US 9,486,524 B2
(45) Date of Patent: Nov. 8, 2016

(54) COMPOSITION FOR ELICITING A SPECIFIC CTL RESPONSE, COMPRISING A LYMPHO-ABLATIVE COMPOUND AND A MOLECULE THAT CONTAINS ANTIGENIC SEQUENCES AND TARGETS PROFESSIONAL ANTIGEN PRESENTING CELLS

(75) Inventors: Xavier Preville, Pins-Justaret (FR); Benedikt Timmerman, Toulouse (FR)

(73) Assignee: GENTICEL, Labege (FR)

( * ) Notice: Subject to any disclaimer, the term of this patent is extended or adjusted under 35 U.S.C. 154(b) by 1162 days.

(21) Appl. No.: 12/310,544

(22) PCT Filed: Aug. 31, 2007

(86) PCT No.: PCT/EP2007/059140
§ 371 (c)(1),
(2), (4) Date: Feb. 27, 2009

(87) PCT Pub. No.: WO2008/025848
PCT Pub. Date: Mar. 6, 2008

(65) Prior Publication Data
US 2011/0097337 A1    Apr. 28, 2011

Related U.S. Application Data

(60) Provisional application No. 60/841,531, filed on Sep. 1, 2006.

(51) Int. Cl.
| | | |
|---|---|---|
| A61K 39/385 | (2006.01) | |
| A61K 45/06 | (2006.01) | |
| A61K 38/16 | (2006.01) | |
| A61K 38/51 | (2006.01) | |
| A61K 39/00 | (2006.01) | |
| A61K 47/48 | (2006.01) | |

(52) U.S. Cl.
CPC ............ *A61K 45/06* (2013.01); *A61K 38/164* (2013.01); *A61K 38/51* (2013.01); *A61K 39/0005* (2013.01); *A61K 47/4833* (2013.01); *A61K 47/48261* (2013.01)

(58) Field of Classification Search
None
See application file for complete search history.

(56) References Cited

U.S. PATENT DOCUMENTS

| | | | | |
|---|---|---|---|---|
| 4,364,935 | A * | 12/1982 | Kung et al. | 530/388.75 |
| 2004/0067905 | A1* | 4/2004 | Krieg | 514/44 |
| 2008/0014211 | A1* | 1/2008 | Bot et al. | 424/185.1 |
| 2008/0152665 | A1* | 6/2008 | Leclerc et al. | 424/185.1 |

FOREIGN PATENT DOCUMENTS

| | | |
|---|---|---|
| EP | 1 576 967 | 9/2007 |
| WO | WO 2005/042109 | 5/2005 |
| WO | WO 2005/053738 | 6/2005 |
| WO | WO 2005089792 A1 * | 9/2005 |

OTHER PUBLICATIONS

Yang et al., J Immunol 2004;172;4599-4608.*
Beiras-Fernandez et al., Experi. And Clin. Transplant., vol. 1, No. 2, Dec. 2003.*
Somerville (Journal of Pharmacy Practice 2003. 16;6:388-400).*
Terando et al., Cancer Immunol Immunother (2003) 52: 680-685.*
Zuckermann et al. (Transplantation. May 15, 2000;69(9):1890-8).*
Bonnefoy-Berard et al. (Transplantation 1991; 51: 669).*
Rebellato et al. (Transplantation 1994; 57: 685).*
Bourdage et al. (Transplantation 1995; 59: 1194).*
Michallet et al. (Transplantation 2003; 75: 657).*
Janeway et al., Immunobiology, 3rd Ed., Garland Science, pp. 6:1-6:9, (1997).*
Anderson et al., Immunol Today. Oct. 1999;20(10):463-8.*
Reinherz et al., Proc. Natl. Acad. Sci., vol. 77, No. 3, pp. 1588-1592, Mar. 1980.*
LaCorcia et al. (Transplantation 2009;87: 966-974).*
Clarke et al., Cancer Res 1998;58:1469-1477.*
Rosenberg et al., Nature Medicine, vol. 10, No. 9, Sep. 2004, pp. 909-915.*
Beyer et al. (Blood. 2005;106:2018-2025).*
Ghiringhelli et al., (Eur. J. Immunol. 2004. 34: 336-344).*
di Paolo et al. (Cancer Res 2006; 66(2): 960-9).*
Krieg (Nat Rev Drug Discov. Jun. 2006;5(6):471-84).*
Gupta et al. (Vaccine, vol. 13, No. 14, pp. 1263-1276, 1995).*
Multhoff et al. (Handb Exp Pharmacol. 2006;(172):279-304).*
Whitmore et al. (Cancer Res. Aug. 15, 2004;64(16):5850-60).*
Awwad, M., et al., "Cyclophosphamide-induced immunologically mediated regression of a cyclophosphamide-resistant murine tumor: a consequence of eliminating precursor L3T4+ suppressor T-cells," Cancer Res., 1989, pp. 1649-1654, vol. 49.
Berd, D., et al., "Induction of cell-mediated immunity to autologous melanoma cells and regression of metastases after treatment with a melanoma cell vaccine preceded by cyclophosphamide," Cancer Res., 1986, pp. 2572-2577, vol. 46.

(Continued)

*Primary Examiner* — Zachary Skelding
(74) *Attorney, Agent, or Firm* — Foley & Lardner LLP

(57) ABSTRACT

The present invention relates to a composition for eliciting a specific cytotoxic T lymphocyte (CTL) response against T cell epitopes in a mammal, which comprises a compound provoking lymphocytopenia, a molecule having selective affinity for professional antigen presenting cells (APC), wherein said molecule is associated to said T cell epitope, and optionally, a pharmaceutical acceptable carrier. Advantageously, the composition further contains an adjuvant. Said composition may be used in anti-infections and anti-cancer therapies.

6 Claims, 10 Drawing Sheets

(56) References Cited

OTHER PUBLICATIONS

Berd, D., et al., "Treatment of metastatic melanoma with an autologous tumor-cell vaccine: clinical and immunologic results in 64 patients," J Clin Oncol., 1990, pp. 1858-1867, vol. 8.
Berd, D., et al., "Immunization with haptenized, autologous tumor cells induces inflammation of human melanoma metastases," Cancer Res., 1991, pp. 2731-2734, vol. 51.
Hengst, J. C., et al., "Cooperation between cyclophosphamide tumoricidal activity and host antitumor immunity in the cure of mice bearing large MOPC-315 tumors," Cancer Res., 1981, pp. 2163-2167, vol. 41.
Reissmann, T., et al., "Augmentation of host antitumor immunity by low doses of cyclophosphamide and matosfamide in two animal tumor models," Cancer Immunol Immunother, 1989, pp. 179-184, vol. 28.
Sahasrabudhe, D. M., et al., "Specific immunotherapy with suppressor function inhibition for metastatic renal cell carcinoma," J Biol Response Mod, 1986, pp. 581-594, vol. 5.
Ben-Efraim, S., et al., "Increase in the effectiveness of melphalan therapy with progression of MOPC-315 plasmacytoma tumor growth," Cancer Cancer Immunol Immunother, 1983, pp. 101-107, vol. 15.
Nagarkatti, M., et al., "Immunomodulation by various nitrosoureas and its effect on the survival of the murine host bearing a syngeneic tumor," Cancer Res., 1989, pp. 6587-6592, vol. 49.
North, R. .T., et al., "Elimination of cycling CD4+ suppressor T cells with an anti-mitotic drug releases non-cycling CD8+ T cells to cause regression of an advanced lymphoma," Immunology, 1990, pp. 90-95, vol. 71.
Morikawa, K., et al., "Hostmediated therapeutic effects produced by appropriately timed administration of bleomycin on a rat fibrosarcoma," Cancer Res., 1985, pp. 1502-1506, vol. 45.
Chun, H. G., et al., "Fludarabine phosphate: a synthetic purine antimetabolite with significant activity against lymphoid malignancies," J Clin Oncol, 1991, pp. 175-188, vol. 9.
Cheson, B. D., "Infectious and immunosuppressive complications of purine analog therapy," J Clin Oncol, 1995, pp. 2431-2448, vol. 13.
Frank, D. A., et al., "Fludarabine-induced immunosuppression is associated with inhibition of STAT1 signaling," Nat Med, 1999, pp. 444-447, vol. 5.
Ladant, D., et al., "Bordetella pertussis adenylate cyclase: a toxin with multiple talents," Trends Microbiol, 1999, pp. 172-176, vol. 7.
Moron, G., et al. "New tools for antigen delivery to the MHC class I pathway," Trends in Immunology, 2004, pp. 92-97, vol. 25.
Guermonprez, P., et al., "The adenylate cyclase toxin of Bordetella pertussis binds to target cells via the alpha(M)beta(2) integrin (CDI Ib/CD18)," J Exp Med, 2001, pp. 1035-1044, vol. 193.
Guermonprez, P., et al., "In vivo receptor-mediated delivery of a recombinant invasive bacterial toxoid to CDI Ic + CD8 alpha —CDI Ibhigh dendritic cells," Eur J Immunol, 2002, pp. 3071-3081, vol. 32.
Fayolle, C., et al. "Therapy of murine tumors with recombinant Bordetella pertussis adenylate cyclase carrying a cytotoxic T cell epitope," J Immunol, 1999, pp. 4157-4162, vol. 162.
Fayolle, C, et al. "Delivery of multiple epitopes by recombinant detoxified adenylate cyclase of Bordetella pertussis induces protective antiviral immunity," J Virol, 2001, pp. 7330-7338, vol. 75.
Preville, X., et al. "Eradication of established tumors by vaccination with recombinant Bordetella pertussis adenylate cyclase carrying the human papillomavirus 16 E7 oncoprotein," Cancer Res, 2005, pp. 641-649, vol. 65.
Rosenberg, S. A., et al. "Cancer immunotherapy: moving beyond current vaccines," Nat Med, 2004, pp. 909-915, vol. 10.
Starzl, T. E., et al. "The clinical use of antilymphocyte globulin in renal homotransplantations," Transplantation, 1967, pp. 1100-1105, Suppl. 5.
Storb, R., et al. "Treatment of established human graft-versus-host disease by antithymocyte globulin," Blood, 1974, pp. 56-75, vol. 44.

Marsh, J., et al., "Prospective randomized multicenter study oomparing cyclosporin alone versus the combination of antithyrnocyte globulin and cyclosporin for treatment of patients with nonscvcre aplastic anemia: a report from the European Blood and Marrow Transplant (EBMT) Severe Aplastic Anaemia Working Party," Blood, 1999, pp. 2191-2195, vol. 93.
Ringden, O., et al., "Low incidence of acute graft-versus-host disease, using unrelated HLA-A-, HLA-B-, and HLA-DR- compatible donors and conditioning, including anti-T-cell antibodies," Transplantation, 1998, pp. 620-625, vol. 66.
Aversa, F., et al., "Treatment of high-risk acute leukemia with T-cell-depleted stem cells from related donors with one fully mismatched HLA haplotype," N Engl J Med, 1998, pp. 1186-1193, vol. 339.
Preville, X., et al., "Mechanisms involved in antithymocyte globulin immuno suppressive activity in a nonhuman primate model," Transplantation, 2001, pp. 460-468, vol. 71.
Preville, X., et al., "A quantitative flow cytometry assay for the preclinical testing and pharmacological momitoring of rabbit antilymphocyte globulins (rATG)," Journal of Immunological Methods, 2000, pp. 45-54, vol. 245.
Gmira, S., et al., "Characterization of recombinant Bordetella pertussis adenylate cyclase toxins carrying passenger proteins," Res Microbiol, 2001, pp. 889-900, vol. 152.
El-Azami-El-Idrissi, M., et al., "Interaction of Bordetella pertussis adenylate cyclase with CDI Ib/CD18: Role of toxin acylation and identification of the main integrin interaction domain," J Biol Chen, 2003, pp. 38514-38521, vol. 278.
Ullenhag, G. J., et al., "Functional HLA-DR T cell epitopes of CEA identified in patients with colorectal carcinoma immunized with the recombinant protein CEA," Cancer Immunol Immunother, 2004, pp. 331-337, vol. 53.
Greiner, J. W., et al., "Vaccine-based therapy directed against carcinoembryonic antigen demonstrates antitumor activity on spontaneous intestinal tumors in the absence of autoimmunity," Cancer Res, 2002, pp. 6944-6951, vol. 62.
Mennuni, C., et al., "Efficient induction of T-cell responses to careinoembryonic antigen by a heterologous prime-boost regimen using DNA and adenovirus vectors carrying a codon usage optimized cDNA," Int J Cancer, 2005, pp. 444-455, vol. 777.
El Azami El Idrissi, M., et al., "The adenylate cyclase of Bordetella pertussis: a vector to target antigen presenting cells," Toxicon, 2002, pp. 1661-1665, vol. 40.
Dudley, M. E., et al., "Cancer regression and autoimmunity in patients after clonal repopulation with antitumor lymphocytes," Science, 2002, pp. 850-854, vol. 298.
Dudley, M. E., et al., "Adoptive cell transfer therapy following non-myelo ablative but lymphodepleting chemotherapy for the treatment of patients with refractory metastatic melanoma," J Clin Oncol, 2005, pp. 2346-2357, vol. 23.
Gattinoni, L., et al., "Adoptive immunotherapy for cancer: building on success," Nat Rev Immunol, 2006, pp. 383-393, vol. 6.
Keating, M. J., et al., "Fludarabine: a new agent with major activity against chronic lymphocytic leukemia," Blood, 1989, pp. 19-25, vol. 74.
Boldt, D. H., et al., "Effects on human peripheral lymphocytes of in vivo administration of 9-beta-D-arabinofuranosyl-2- fluoroadcninc-5 'monophosphate (NSC 312887), a new purine antimetabolite," Cancer Res, 1984, pp. 4661-4666, vol. 44.
Kuwatani, M., et al., "An irradiation-free nonmyeloablative bone marrow transplantation model: importance of the balance between donor T-cell number and the intensity of conditioning," Transplantation, 2005, pp. 1145-1152, vol. 80.
Petrus, M. J., et al., "An immuno ablative regimen of fludarabine and cyclophosphamide prevents fully MHC-mismatched murine marrow graft rejection independent of GVHD," Biol Blood Marrow Transplant, 2000, pp. 182-189, vol. 6.
Berenson, J. R., et al., "Syngeneic adoptive immunotherapy and chemoimmunotherapy of a Friend leukemia: requirement for T cells," J Immunol, 1975, pp. 234-238, vol. 115.
Eberlein, T. J., et al., "Regression of a disseminated syngeneic solid tumor by systemic transfer of lymphoid cells expanded in interleukin 2," J Exp Med, 1982, pp. 385-397, vol. 156.

(56) References Cited

OTHER PUBLICATIONS

North, R. J., "Cyclophosphamide-facilitated adoptive immunotherapy of an established tumor depends on elimination of tumor-induced suppressor T cells," J Exp Med, 1982, pp. 1063-1074, vol. 155.

Rosenberg, S. A., et al., "A new approach to the adoptive immunotherapy of cancer with tumor-infiltrating lymphocytes," Science, 1986, pp. 1318-1321, vol. 233.

Badovinac, V. P., et al., "Accelerated CD8+ T-cell memory and prime-boost response after dendritic-cell vaccination," Nat Med, 2005, pp. 748-756, vol. 11.

Robbins, P. F., et al., "Transduction and Expression of the Human Carcinoembryonic Antigen Gene in a Murine Colon Carcinoma Cell Line," Cancer Res, 1991, pp. 3657-3662, vol. 51.

International Search Report, issued on Feb. 14, 2008, for International Application No. PCT/EP2007/059140.

Mackova et al., "Prime/boost immunotherapy of HPV16-induced tumors with E7 protein delivered by *Bordetella* adenylate cyclase and modified vaccinia virus Ankara," Cancer Immunology Immunotherapy, vol. 55, No. 1, Jan. 1, 2006.

Hauser et al., "Secretory heat-shock protein as a dendritic cell-targeting molecule: a new strategy to enhance the potency of genetic vaccines," *Gene Therapy*, vol. 11, 2004, pp. 924-932.

Feng et al., "Exogenoous stress proteins enhance the immunogenicity of apoptotic tumor cells and stimulate antitumor immunity," *Blood*, vol. 101, No. 1, Jan. 1, 2003, pp. 245-252.

Hentschke, et al., "Reduced intensity conditioning regimens: Low-intensity conditioning and hematopoietic stem cell transplantation in patients with renal and colon carcinoma", *Bone Marrow Transplantation*, 2003, vol. 31, pp. 253-261.

\* cited by examiner

SEQUENCE LISTING

```
<160> NUMBER OF SEQ ID NOS: 16

<210> SEQ ID NO 1
<211> LENGTH: 18
<212> TYPE: DNA
<213> ORGANISM: Artificial sequence
<220> FEATURE:
<223> OTHER INFORMATION: Primer CEA1

<400> SEQUENCE: 1
accatcaccg tctctgcg                                                   18

<210> SEQ ID NO 2
<211> LENGTH: 28
<212> TYPE: DNA
<213> ORGANISM: Artificial sequence
<220> FEATURE:
<223> OTHER INFORMATION: Primer CEA2

<400> SEQUENCE: 2
gggcactagt ggtcagggta cggttgcc                                        28

<210> SEQ ID NO 3
<211> LENGTH: 31
<212> TYPE: DNA
<213> ORGANISM: Artificial sequence
<220> FEATURE:
<223> OTHER INFORMATION: Primer CEA3

<400> SEQUENCE: 3
gggcaccggt aatggtatcc cgcagcaaca c                                    31

<210> SEQ ID NO 4
<211> LENGTH: 42
<212> TYPE: DNA
<213> ORGANISM: Artificial sequence
<220> FEATURE:
<223> OTHER INFORMATION: Primer CEA4

<400> SEQUENCE: 4
cgcagagacg gtgatggtgt taacggcacc cgcagacaga cc                        42

<210> SEQ ID NO 5
<211> LENGTH: 29
<212> TYPE: DNA
<213> ORGANISM: Artificial sequence
<220> FEATURE:
<223> OTHER INFORMATION: Primer CEA5
```

<400> SEQUENCE: 5
gggcgctagc cgtctgcagc tgtccaatg                               29

<210> SEQ ID NO 6
<211> LENGTH: 29
<212> TYPE: DNA
<213> ORGANISM: Artificial sequence
<220> FEATURE:
<223> OTHER INFORMATION: Primer CEA6

<400> SEQUENCE: 6
cccgggtacc cggcgtgatt ttggcgata                               29

<210> SEQ ID NO 7
<211> LENGTH: 26
<212> TYPE: DNA
<213> ORGANISM: Artificial sequence
<220> FEATURE:
<223> OTHER INFORMATION: Primer CEA7 for production and purification of
      recombinant CEAA3B3 protein

<400> SEQUENCE: 7
gcggccgcac catcaccgtc tctgcg                                  26

<210> SEQ ID NO 8
<211> LENGTH: 28
<212> TYPE: DNA
<213> ORGANISM: Artificial sequence
<220> FEATURE:
<223> OTHER INFORMATION: Primer CEA8 for production and purification of
      recombinant CEAA3B3 protein

<400> SEQUENCE: 8
cccgctcgag ggcacccgca gacagacc                                28

<210> SEQ ID NO 9
<211> LENGTH: 22
<212> TYPE: DNA
<213> ORGANISM: Artificial sequence
<220> FEATURE:
<223> OTHER INFORMATION: Primer CyaA delta 1

<400> SEQUENCE: 9
gggcgagctc tggggccacg at                                      22

<210> SEQ ID NO 10
<211> LENGTH: 24
<212> TYPE: DNA
<213> ORGANISM: Artificial sequence
<220> FEATURE:
<223> OTHER INFORMATION: Primer CyaA delta 2

<400> SEQUENCE: 10
actagtgcct cgatcccgaa gccg                                    24

<210> SEQ ID NO 11
<211> LENGTH: 24
<212> TYPE: DNA
<213> ORGANISM: Artificial sequence
<220> FEATURE:
<223> OTHER INFORMATION: Primer CyaA delta 3

<400> SEQUENCE: 11
actagtcatg ctgtatggcg acgc                                    24

```
<210> SEQ ID NO 12
<211> LENGTH: 22
<212> TYPE: DNA
<213> ORGANISM: Artificial sequence
<220> FEATURE:
<223> OTHER INFORMATION: Primer CyaA delta 4

<400> SEQUENCE: 12
cccggcatgc gcgccggtct gg                                              22

<210> SEQ ID NO 13
<211> LENGTH: 432
<212> TYPE: DNA
<213> ORGANISM: Artificial sequence
<220> FEATURE:
<223> OTHER INFORMATION: DNA fragment corresponding to CyaA amino acid
      sequence 1149 to 1356

<400> SEQUENCE: 13
caacgagctc tggggccacg atggcaacga cacgatacgc ggccggggcg gcgacgacat      60
cctgcgcggc ggcctgggcc tggacacgct gtatggcgag gacggcaacg acatcttcct    120
gcaggacgac gagaccgtca gcgatgacat cgacggcggc gcggggctgg acaccgtcga    180
ctactccgcc atgatccatc caggcaggat cgttgcgccg catgaatacg gcttcgggat    240
cgaggccatg ctgtatggcg acgccggcaa cgacaccctc tacggggggc tgggcgacga    300
tacccttgaa ggcggcgcgg gcaacgattg gttcggccag acgcaggcgc gcgagcatga    360
cgtgctgcgc ggcggagatg gggtggatac cgtcgattac agccagaccg gcgcgcatgc    420
cggcattgcc gc                                                        432

<210> SEQ ID NO 14
<211> LENGTH: 29
<212> TYPE: DNA
<213> ORGANISM: Artificial sequence
<220> FEATURE:
<223> OTHER INFORMATION: Primer CEA7 for production and purification of
      recombinant CEA protein

<400> SEQUENCE: 14
aatctcgagg atcagcgcaa caccaacca                                       29

<210> SEQ ID NO 15
<211> LENGTH: 24
<212> TYPE: DNA
<213> ORGANISM: Artificial sequence
<220> FEATURE:
<223> OTHER INFORMATION: Primer CEA8 for production and purification of
      recombinant CEA protein

<400> SEQUENCE: 15
atatccatgg agtctccgtc tgcc                                            24

<210> SEQ ID NO 16
<211> LENGTH: 20
<212> TYPE: DNA
<213> ORGANISM: Artificial sequence
<220> FEATURE:
<223> OTHER INFORMATION: ODN1826 sequence

<400> SEQUENCE: 16
tccatgacgt tcctgacgtt                                                 20
```

COMPOSITION FOR ELICITING A SPECIFIC CTL RESPONSE, COMPRISING A LYMPHO-ABLATIVE COMPOUND AND A MOLECULE THAT CONTAINS ANTIGENIC SEQUENCES AND TARGETS PROFESSIONAL ANTIGEN PRESENTING CELLS

FIELD OF THE INVENTION

The present invention relates to a pharmaceutical composition for eliciting a specific cytotoxic T lymphocyte (CTL) response against at least one T cell epitope in a mammal, which comprises:
  a first compound provoking lymphocytopenia;
  as a second compound, a molecule having selective affinity for professional antigen presenting cells (APC), wherein said molecule is associated to said T cell epitope; and
  optionally, a pharmaceutical acceptable carrier.

The invention also relates to a pharmaceutical composition comprising:
  a first compound provoking lymphocytopenia;
  as a second compound, a molecule having selective affinity for APC, wherein said molecule is associated to at least one T cell epitope of an antigen derived from an infectious disease agent; and
  optionally, a pharmaceutical acceptable carrier,
  as a combined preparation for simultaneous, separate or sequential use in the treatment and/or prevention of an infectious disease in a patient.

The invention further relates to a pharmaceutical composition comprising:
  a first compound provoking lymphocytopenia;
  as a second compound, a molecule having selective affinity for APC, wherein said molecule is associated to at least one T cell epitope of an antigen derived from a cellular malignancy, dysplasia, tumour or cancer; and
  optionally, a pharmaceutical acceptable carrier,
  as a combined preparation for simultaneous, separate or sequential use in the treatment and/or prevention of respectively cellular malignancy, dysplasia tumour or cancer in a patient.

BACKGROUND

The ability of anticancer drugs to facilitate the acquisition of antitumor immunity by tumor bearers has been recognized. Several anticancer drugs such as cyclophosphamide (1-7), L-PAM4 (8), 1,3-bis(2-chloroethyl)-1-nitrosourea (9), vinblastine (10), fludarabine and bleomycin (11) have been shown to enhance the acquisition of T cell-mediated antitumor responses in a variety of animal tumor models (1, 5, 6, 8-11) and in patients with advanced melanoma (2-4) or advanced renal carcinoma (7).

Studies into the mechanisms through which the anticancer drugs enhance the acquisition of T cell-dependent tumor-eradicating immunity in tumor bearers revealed that the chemotherapy leads to a shift in the cytokine profile from anti-inflammatory cytokines (such as TGF-β and IL-10) with inhibitory activity for CTL generation toward proinflammatory cytokines (e.g., TNF-α, IFN-7, and GM-CSF) that favor the development of antitumor cell-mediated immunity.

In particular, fludarabine is an immunosuppressive purine analogue that has been used mostly in the treatment of indolent lymphoid malignancies (12). Repeated cycles of fludarabine therapy induce a profound T-cell depletion, particularly of CD4+ T cells (13). Unlike other immunosuppressive cytotoxic drugs, such as cyclophosphamide, fludarabine induces lymphocyte apoptosis in both dividing cells as well as cells in the G0-G1 phase of the cell cycle. This cell cycle independent activity may be attributed to the drug's inhibition of STAT1 signaling (14).

So far immuno-therapy of cancer and chronic infectious diseases has had limited success. The inventors show in the present application that a combination of lympho-ablative drugs with recombinant proteinous vaccines show much more encouraging results.

As lympho-ablative drugs kill (apoptosis) or render lymphocytes inactive (anergic), they are expected to reduce the effectiveness of vaccines that deliver antigens to professional antigen presenting cells.

In particular, the adenylate cyclase (CyaA) of *Bordetella pertussis* has the capacity to deliver its catalytic domain into the cytosol of eukaryotic cells (15). Thus CD4+ and CD8+ T cell epitopes inserted into the catalytic site of CyaA are processed and presented by MHC class II and I molecules, respectively, at the surface of antigen-presenting cells (APC; (16)).

Furthermore, CyaA was shown to bind specifically to the αMβ2 integrin (CD11b/CD18; (17)), and therefore to target these T cell epitopes to the CD11b+dendritic cell subpopulation (18).

Immunization of mice with recombinant CyaAs bearing appropriate T cell epitopes led to the induction of strong CTL responses, full protection against a lethal viral challenge, and efficient prophylactic and therapeutic anti-tumor immunity (19-21).

Despite many encouraging results at the pre-clinical level, translation of adoptive cell-based immunotherapies to the clinic has faced many failures. According to Rosenberg (22), the objective response rate of immunotherapeutic trials in cancer remains below 3%, the better results being obtained with techniques based on autologous adoptive cell transfer therapies. This approach is laborious, expensive and difficult to generalize safely. Hence, it is of interest to specify at the pre-clinical level, strategies to improve adoptive cell-based immunotherapies.

SUMMARY OF THE INVENTION

The invention relates to a method for eliciting in a mammal a specific cytotoxic T lymphocyte (CTL) response against at least one T cell epitope, the method comprising administering to a mammal in need thereof:

a compound provoking lymphocytopenia; and a molecule, with selective affinity for professional antigen presenting cells (APC), which comprises a foreign antigen that bears at least one said T cell epitope.

In an embodiment, the invention relates to a method for inducing a therapeutic immune response in a mammalian patient suffering from a chronic infectious disease, or of a cellular malignancy, dysplasia, tumor or cancer, which method comprises administering to a patient in need thereof:

a composition comprising a compound provoking lymphocytopenia; and a composition comprising a molecule, with selective affinity for professional antigen presenting cells (APC), that bears an antigen of respectively the infectious disease agent or of the cellular malignancy, the dysplasia, the tumor or the cancer.

In an additional embodiment, the invention relates to a pharmaceutical composition for eliciting in a mammal a specific cytotoxic T lymphocyte (CTL) response against at least one T cell epitope or for inducing a therapeutic immune response in a mammalian patient suffering from a chronic infectious disease, or of a cellular malignancy, dysplasia, tumor or cancer, wherein said composition comprises:

a compound provoking lymphocytopenia;

a molecule, with selective affinity for professional antigen presenting cells (APC), which is associated to said at least one T cell epitope or which is associated to an antigen of respectively the infectious disease agent or of the cellular malignancy, the dysplasia, the tumor or the cancer; and optionally, a pharmaceutical acceptable carrier.

In an additional embodiment, the invention relates to a kit for eliciting in a mammal a specific cytotoxic T lymphocyte (CTL) response against at least one T cell epitope or for inducing a therapeutic immune response in a mammalian patient suffering from a chronic infectious disease, or of a cellular malignancy, dysplasia, tumor or cancer, wherein said kit comprises:

a composition comprising a compound provoking lymphocytopenia; and a composition comprising a molecule, with selective affinity for professional antigen (APC), which comprises a foreign antigen that bears at least one said T cell epitope bearing an antigen of respectively the infectious disease agent or of the cellular malignancy, the dysplasia, the tumor or the cancer.

In an additional embodiment, the invention relates to a method for the prevention or for the treatment of an infection in a mammal patient, wherein the agent responsible of said infection expresses a specific antigen containing at least one T cell epitope, said method comprising the administration to a patient in need thereof of a composition comprising:

a compound provoking lymphocytopenia; and a molecule, with selective affinity for professional antigen presenting cells (APC), which comprises a foreign antigen that bears at least one said T cell epitope that comprises said antigen specific of said agent responsible of said infection or at least one T cell epitope contained in said antigen.

In an additional embodiment, the invention relates to a method for the prevention or for the treatment of a cancer in a mammal patient, particularly cancer of the respiratory and digestive tractus, wherein the tumour cells express the human CEA protein, said method comprising the administration to a patient in need thereof of a composition comprising a rabbit or a horse polyclonal anti-lymphocyte or anti-thymocyte antibody (ATG) provoking lymphocytopenia; and in addition a composition comprising a recombinant adenylate cyclase carrying the A3-B3 region of the human CEA protein.

In an additional embodiment, the invention relates to a method for the prevention or for the treatment of a cancer induced by a HPV in a mammal patient, wherein the tumour cells express the E7 oncogene of HPV, said method comprising the administration to a patient in need thereof of:

a composition comprising a rabbit or a horse polyclonal ATG provoking lymphocytopenia; and subsequently a composition comprising a recombinant adenylate cyclase carrying the E7 oncogene from HPV.

Three micrograms of the purified proteins were separated on a 4% to 15% gradient SDS polyacrylamide gel and stained by Coomassie blue. Lane 1, wild-type CyaA; lane 2, CyaA-CEA$_{A3B3}$; lane 3, CyaA$_A$-CEA$_{A3B3}$; lane 4, CEA$_{A3B3}$.

Figure 2:
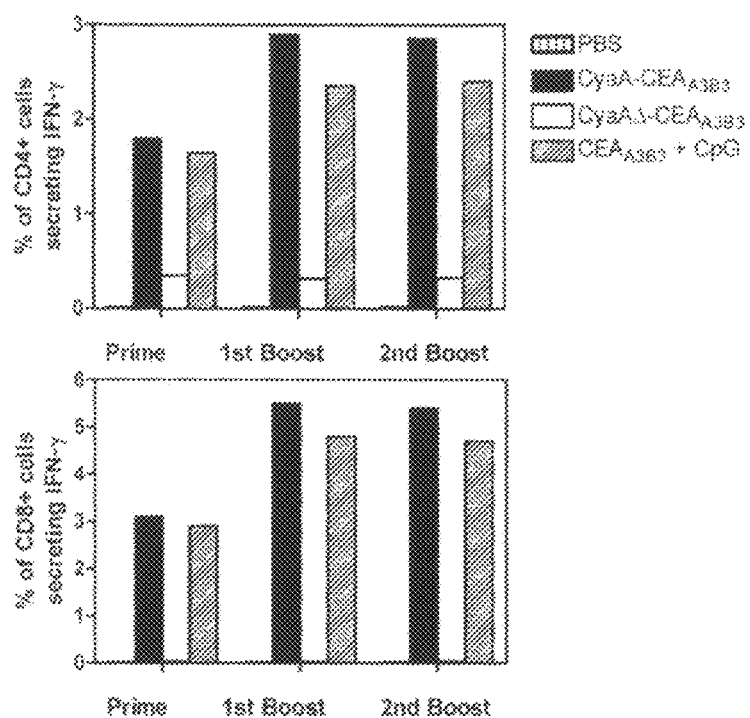

FIG. 2 (example 1): Polarized Th1 response induced by prime-boost immunization with recombinant CEA proteins.

Immunizations performed iv with 50 µg of recombinant CEA proteins were boosted id 7 and 14 days later with 10 µg of similar material. Seven days after last immunization, CEA-specific IFN-γ producing cells were detected by FACS analysis and intracellular cytokine staining. Data are expressed as the median percentages of CD4+ or CD8+ cells expressing IFN-γ (n=3) upon restimulation. Backgrounds results obtained with non-stimulated splenocytes are substracted.

Figure 3:
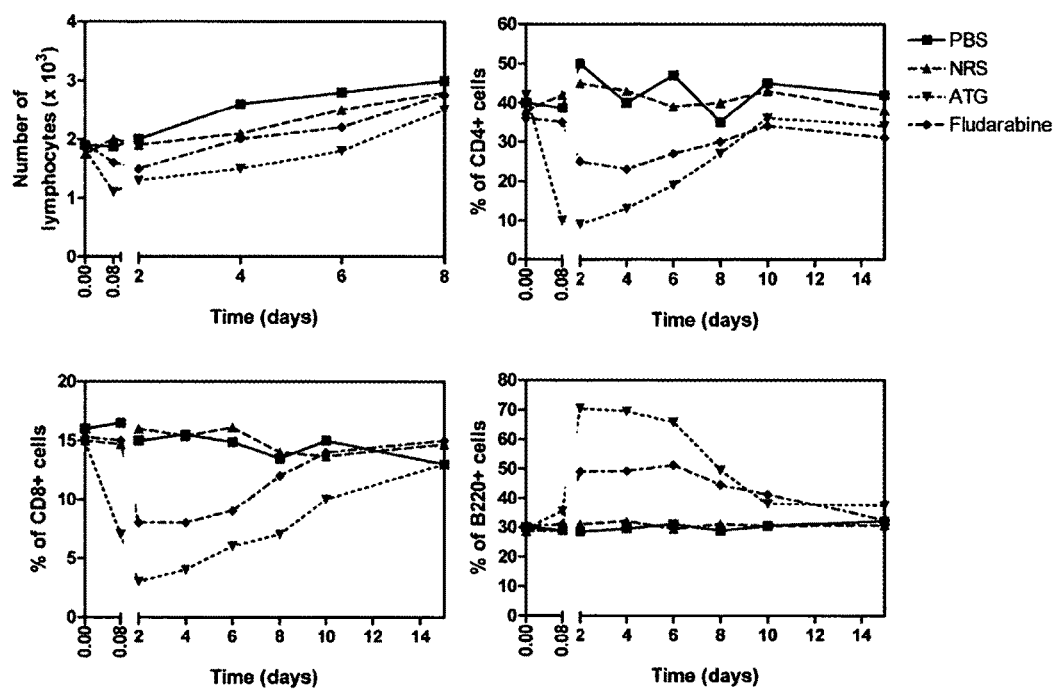

FIG. 3 (example 1): Peripheral blood lymphocyte depletion induced by immunosuppressive treatment Kinetic analysis of the number of lymphocytes in peripheral blood following i.p. injection of 200 mg/kg/day fludarabine for 6 consecutive days or following a single i.p. injection of 20 mg/kg ATG (upper left panel). The three other panels show the kinetic analysis of the percentages of CD4+, CD8+ and B220+ lymphocytes in peripheral blood following above-described immunosuppressive treatment.

Figure 4:
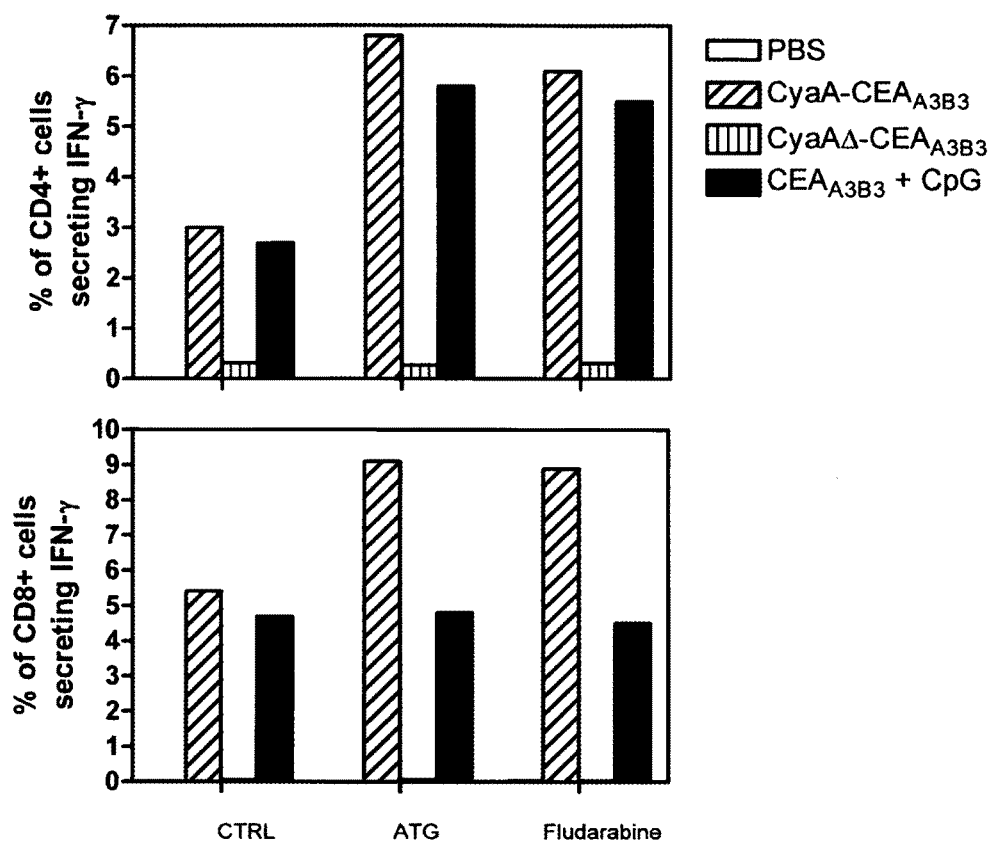

FIG. 4 (example 1): Increased magnitude of CEA-specific Th1 response as a result of immunosuppression and prime-boost immunization.

Fludarabine- or ATG-based immunosuppressive treatments were applied to animals 10 days prior to prime boost immunization with recombinant CEA proteins. Seven days after last immunization, CEA-specific IFN-γ producing cells were detected by FACS analysis and intracellular cytokine staining. Data are expressed as the median percentages of CD4+ or CD8+ cells expressing IFN-γ (n=3) upon restimulation. Backgrounds results obtained with non-stimulated splenocytes are substracted.

FIG. 5 (example 1): Increased survival median following CyaA-CEAA3B3 prime boost immunization as a result or prior lymphoablation.

Fludarabine- or ATG-based immunosuppressive treatments were applied to animals 5 days prior to sc tumor inoculation with 2×10$^4$ B16F0CEA-GFP cells. (A) Three days after tumor cells injection, animals were subjected to prime boost immunization with recombinant CEA proteins. Tumor growth was monitored regularly thereon. Mice were sacrificed when sanitary status commanded. Survival curves are shown. Animals from control setting (CTRL) were not subjected to immunosuppression. (B) Same as in A, but immunotherapy was performed 5 days after tumor injection.

Figure 6:
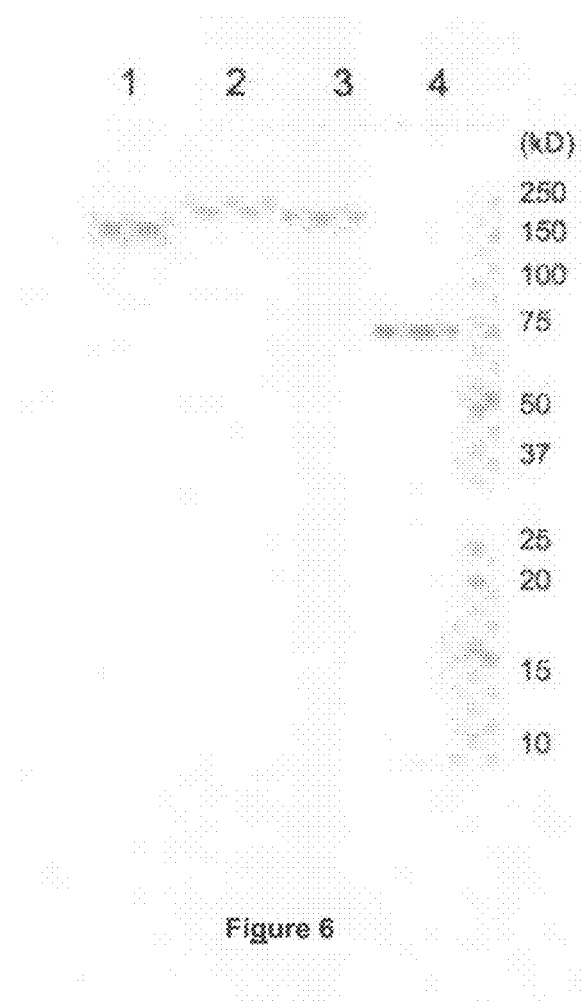

FIG. 6 (example 2): SDS-PAGE analysis of the CEA recombinant proteins

Three micrograms of the purified proteins were separated on a 4% to 15% gradient SDS polyacrylamide gel and stained by Coomassie blue. Lane 1, CyaA-HPV16E7Δ; lane 2, CyaA-CEA$_{A3B3}$; lane 3, CyaA$_A$-CEA$_{A3B3}$; lane 4, His-tag CEA.

Figure 7:
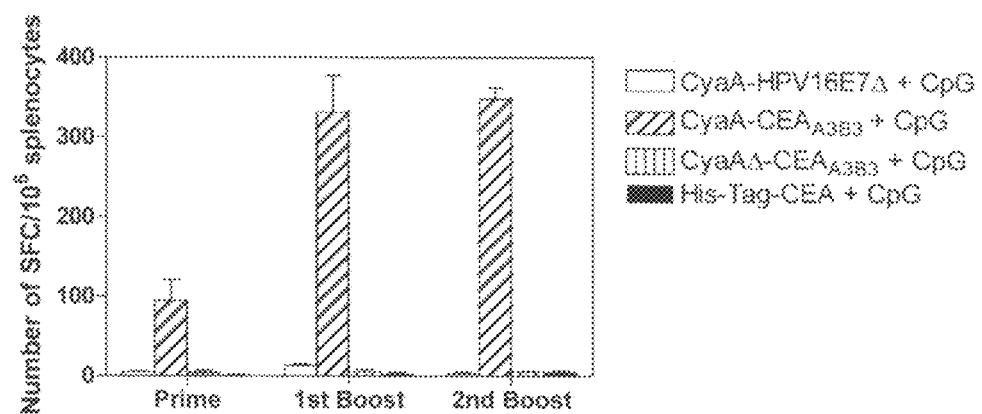

FIG. 7 (example 2): Th1 response induced by prime-boost immunization with recombinant CEA proteins.

Immunizations performed iv with equimolar amounts of indicated recombinant proteins (50 µg for CyaAs, 19.2 µg for His-tag CEA) in presence of 10 µg CpG, were boosted id 7 and 14 days later with 10 µg of similar material (3.8 µg for His-tag CEA) and 2 µg of CpG. Seven days after last immunization, CEA-specific IFN-γ producing CD8+ cells were detected by ex vivo ELISpot assay using 1 µg/ml CEA pepscan. Data are expressed as the median numbers of γ-IFN spot forming colonies, SFC (n=3).

Figure 8:
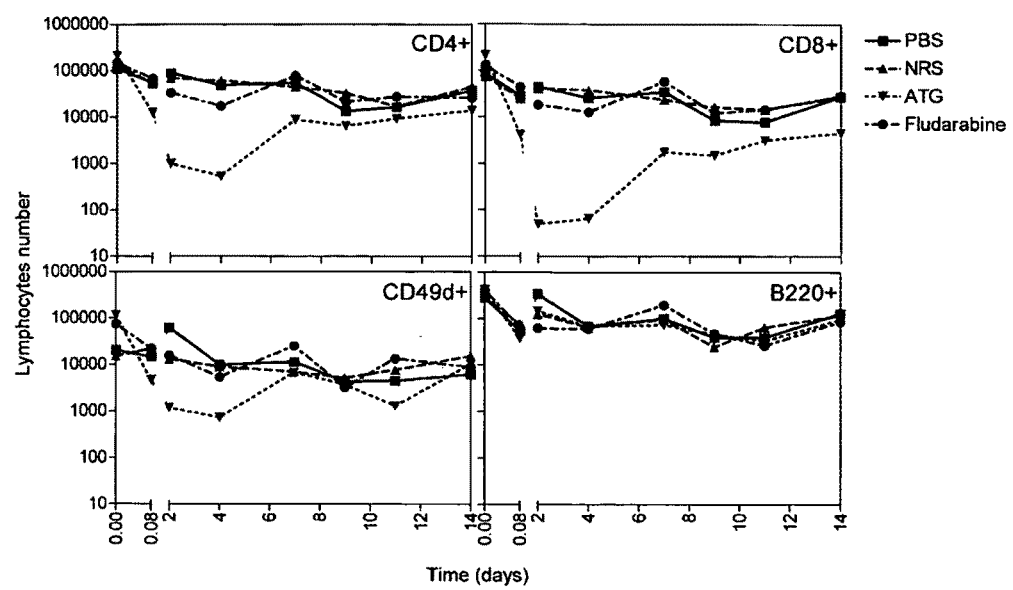

FIG. 8 (example 2): Peripheral blood lymphocyte depletion induced by immunosuppressive treatment.

Kinetic of the number of lymphocytes (CD4+, CD8+, CD49d+ and B220+) in peripheral blood following i.p. injection of 100 mg/kg/day Fludarabine for 6 days or following a single i.p. injection of 20 mg/kg ATG. Controls are injected with PBS or with 20 mg/kg of normal rabbit serum (NRS)

Figure 9:
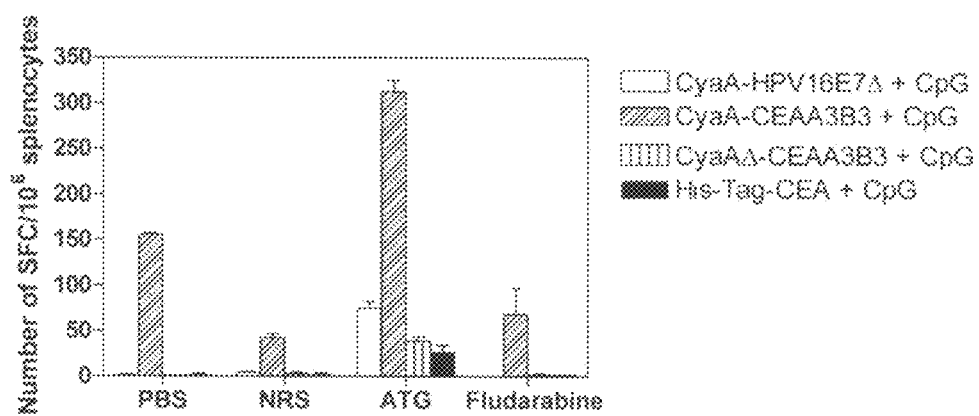

FIG. 9 (example 2): Increased magnitude of CEA-specific Th1 response as a result of immunosuppression and prime-boost immunization.

ATG- or Fludarabine-based immunosuppressive treatments were applied to animals 7 days prior to prime boost immunization with recombinant proteins. Immunizations performed iv with equimolar amounts of indicated recombinant proteins (50 µg for CyaAs, 19.2 µg for His-tag CEA) in presence of 10 µg CpG, were boosted id 7 days later with 10 µg of similar material (3.8 µg for His-tag CEA) and 2 µg of CpG. Seven days after last immunization, CEA-specific IFN-γ producing CD8+ cells were detected by ex vivo ELISpot assay using 1 µg/ml CEA pepscan. Data are expressed as the median numbers of γ-IFN spot forming colonies, SFC (n=2).

Figure 10:
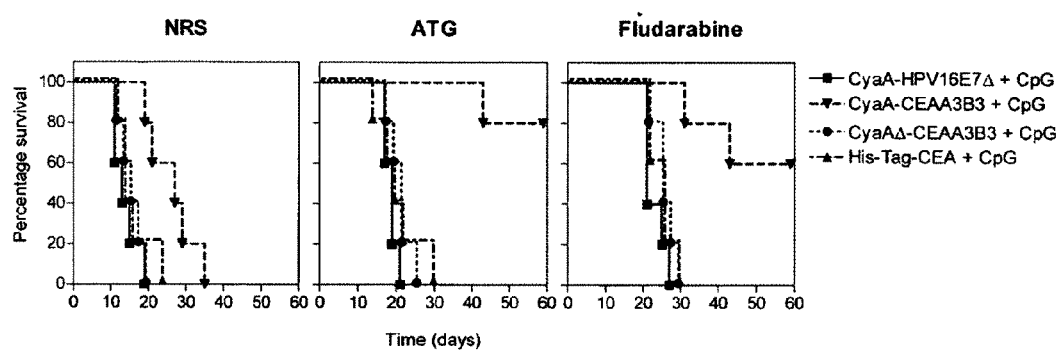

FIG. 10 (example 2): Increased survival median following CyaA-CEA$_{A3B3}$ prime boost immunization as a result or prior lymphoablation.

Tumor inoculation was performed with $5 \times 10^5$ MCa32A cells. Three days later ATG- or Fludarabine-based immunosuppressive treatments were applied. Control animals received normal rabbit serum. Ten days after tumor cells injection (7 after immunosuppression), animals were subjected to prime boost immunization with recombinant proteins. Immunizations performed iv with equimolar amounts of indicated recombinant proteins (50 µg for CyaAs, 19.2 µg for His-tag CEA) in presence of 10 µg CpG, were boosted id 7 days later with 10 µg of similar material (3.8 µg for His-tag CEA) and 2 µg of CpG. Tumor growth was monitored regularly thereon. Mice were sacrificed when sanitary status commanded. Survival curves are shown.

DETAILED DESCRIPTION

The inventors have now discovered that the potentiating effect of lympho-ablative agents such as anti-thymocyte immunoglobulin (ATG) or fludarabine to facilitate the acquisition of therapeutic immunity by the patient, is substantially enhanced if the antigen(s) in the drug formulation are targeted to professional antigen presenting cells (APC) in vivo upon administration.

Vaccine vectors that target professional antigen presenting cells (APC) such as macrophages, neutrophils and dendritic cells have the advantage of selective delivery of antigens to these APC's, as result of a specific binding affinity for a cell surface factor of the APC's, resulting in stronger antigen-specific T cell responses (helper and/or cytotoxic). However in combination of lympho-ablative compounds this would be expected not to be the case as the final target population of lymphocytes are affected, reduced, diminished or rendered anergic (=non-functional) by said lympho-ablative compounds.

The inventors show that when an antigen is targeted to APC's in vivo by a protein vector, the adenylate cyclase (CyaA) which has high affinity for the CD11b molecule (specifically present on APC such as dendritic cells, macrophages and also on neutrophils), surprisingly they have a much stronger CTL induction that if no ATG-mediated lympho-ablative treatment is made. This was unexpected.

The inventors show that upon ATG-mediated lympho-ablative treatment, this stronger CTL induction is associated with an ability to better prevent tumor growth in vivo. The inventors also show that fludarabine-mediated lympho-ablative treatment also inhibits tumor growth. This property facilitates the ability of CyaA-based immunotherapy to better prevent tumor growth in vivo.

The inventors have furthermore shown that such enhancements are not simply due to the use of immuno-ablative compounds such as ATG or Fludarabine, but are actually due to the CD11b targeting potential of the CyaA-based vector and can be extrapolated to other systems that target APC's such as Heat Shock Proteins. This conclusion can be drawn because of three reasons:

1. The CyaA vector deleted for its CD11b binding motif on APC's, no longer targets APC's, and is not only less active than the CyaA vector but in addition does not measurably improve the induction of an immune response against the inserted foreign antigen (CEAA3B3) when the tested animals were priory treated with an immuno-depletory compound: ENHANCEMENT BY THE CD11b—TARGETING FUNCTION of the vaccine.

2. The CEA antigen without the molecule having selective affinity for APC, adjuvanted with CpG or with Poly ICLC or with Monophosphoryl A, induces a significant immune response against CEA depending on the technique used to detect immunogenicity. In contrast, when the tested animals were priory treated with an immuno-depletory compound, the induction of an immune response against the foreign antigen (CEA) does not measurably improve:NO ENHANCEMENT BY ADJUVANT THAT DOES NOT TARGET SPECIFIC CELLS.

3. The inventors have preliminary evidence suggesting that a comparable immuno-potentiation can be obtained with a fusion protein of Hsp65 with CEAA3B3. The Hsp65 protein vector carrying CEAA3B3, targets APC by recognition of its Toll-Like Receptors (TLR4) on the surface: ENHANCEMENT BY THE APC TARGETING FUNCTION of the vaccine.

Consequently, in one aspect the present invention relates to a pharmaceutical composition for eliciting a specific cytotoxic T lymphocyte (CTL) response against at least one T cell epitope in a mammal, which comprises:
  a first compound provoking lymphocytopenia;
  as a second compound, a molecule having selective affinity for professional antigen presenting cells (APC), wherein said molecule is associated to said T cell epitope; and
  optionally, a pharmaceutical acceptable carrier.

Advantageously, the first compound is capable of provoking transient T cell depletion. More advantageously, the first compound is selected from the group consisting of polyclonal anti-lymphocyte and anti-thymocyte immunoglobulins (ATG) such as rabbit or horse polyclonal anti-lymphocyte and anti-thymocyte immunoglobulins (ATG), purine, pyrimidine analogs, alkylating agents, monoclonal and polyclonal antibodies capable of the peripheral and/or central depletion of T, B and NK lymphocytes. It may be fludarabine or cyclophosphamide. The antibodies capable of depleting lymphocytes are selected from the group consisting of anti-CD8, anti-CD4, anti-CD25, anti-CD3 and anti-CD52 monoclonal antibodies.

In a particular embodiment, the molecule having selective affinity for APC is selected from the group consisting of adenylate cyclases, heat shock proteins (HSP), shigatoxin and LAG-3. Preferably, the adenylate cyclase is from *Bordetella pertussis*, the HSP is selected from the group consisting of hsp65 and hsp70, said hsp65 and hsp70 being advantageously from *Mycobacterium bovis*, and said shigatoxin is from *Shigella dysenteriae*.

In a preferred embodiment, the pharmaceutical composition according to the invention further comprises an adjuvant. Adjuvants are well known from the skilled person and may be used indifferently in the present invention. It may be advantageously a toll-like receptor (TLR) ligand of class 3 (e.g. poly-ICLC), a TLR-9 ligand (e.g. CpG) or a TLR-4 ligand (e.g. monophosphoryl-A), and more advantageously the CpG adjuvant of sequence SEQ ID NO 16 wherein the bases are phosphorothioate. Said adjuvant is preferably in solution with the second compound.

In a further preferred embodiment, the molecule having selective affinity for APC is covalently coupled to said at least one T cell epitope. Advantageously, the molecule having selective affinity for APC and said at least one T cell epitope are polypeptides encoded by DNA sequences fused by recombinant DNA technology.

In the pharmaceutical composition according to the invention, said T cell epitope is from an antigen derived from an infectious disease agent or from a cellular malignancy, dysplasia, tumour or cancer. Preferably, the infectious disease agent is selected from the group consisting of human papilloma virus (HPV), human immunodeficiency virus (HIV), hepatitis B virus (HBV), hepatitis C virus (HCV), *Chlamydia trachomatis* and *Mycobacterium tuberculosis*. Also preferably, the antigen derived from the cellular malignancy, dysplasia, tumour or cancer is selected from the group consisting of carcino-embryonic antigen (CEA), MAGE-A3, telomerase (TERT), E7 oncogene from the human papilloma virus (HPV) and P53.

The invention also relates to the pharmaceutical composition as described above for use as a prophylactic or therapeutic vaccine.

In a preferred embodiment, the mammal is a human.

The pharmaceutical composition according to the invention is advantageously formulated for intramuscular, intravenous, intradermal, cutaneous, subcutaneous, intraperitoneal, mucosal or oral administration.

The invention further relates to a pharmaceutical composition comprising :

- a first compound provoking lymphocytopenia;
- as a second compound, a molecule having selective affinity for APC, wherein said molecule is associated to at least one T cell epitope of an antigen derived from an infectious disease agent; and
- optionally, a pharmaceutical acceptable carrier, as a combined preparation for simultaneous, separate or sequential use in the treatment and/or prevention of an infectious disease in a patient.

In a preferred embodiment of the combined preparation, the first compound is administered before the second compound. Advantageously, the second compound is in solution with an adjuvant. Advantageously, the adjuvant is a toll-like receptor (TLR) ligand selected from the group consisting of TLR ligands of class 3 such as poly-ICLC, TLR ligands of class 9 such as CpG and TLR ligands of class 4 such as monophosphoryl-A.

The invention also relates to a pharmaceutical composition comprising :

- a first compound provoking lymphocytopenia;
- as a second compound, a molecule having selective affinity for APC, wherein said molecule is associated to at least one T cell epitope of an antigen derived from a cellular malignancy, dysplasia, tumour or cancer; and
- optionally, a pharmaceutical acceptable carrier, as a combined preparation for simultaneous, separate or sequential use in the treatment and/or prevention of respectively cellular malignancy, dysplasia tumour or cancer in a patient.

In a preferred embodiment of the combined preparation, the first compound is administered before the second compound. Advantageously, the second compound is in solution with an adjuvant. Advantageously, the adjuvant is a toll-like receptor (TLR) ligand selected from the group consisting of TLR ligands of class 3 such as poly-ICLC, TLR ligands of class 9 such as CpG and TLR ligands of class 4 such as monophosphoryl-A.

Advantageously, the pharmaceutical composition according to the invention is for use in the treatment and/or prevention of a cancer wherein the cancer cells express the human CEA protein, advantageously cancer of the respiratory and digestive tractus, wherein the first compound is a rabbit or a horse polyclonal ATG and the second compound is a recombinant adenylate cyclase carrying the A3-B3 region of the human CEA protein.

In another advantageous embodiment, the pharmaceutical composition according to the invention is for use in the treatment and/or prevention of a cancer wherein the cancer cells express the CEA protein such as the human CEA protein, advantageously cancer of the respiratory and digestive tractus, wherein the first compound is fludarabine and the second compound is a recombinant adenylate cyclase carrying the A3-B3 region of the human CEA protein.

In another advantageous embodiment, the pharmaceutical composition according to the invention is for use in the treatment and/or prevention of a cancer induced by HPV wherein the cancer cells express the E7 oncogene of HPV, wherein the first compound is a rabbit or a horse polyclonal ATG and the second compound is a recombinant adenylate cyclase carrying the E7 oncogene of HPV.

Alternately, the pharmaceutical composition according to the invention is for use in the treatment and/or prevention of a cancer induced by HPV wherein the cancer cells express the E7 oncogene of HPV, wherein the first compound is fludarabine and the second compound is a recombinant adenylate cyclase carrying the E7 oncogene of HPV.

The invention also relates to a method for eliciting in a mammal a specific cytotoxic T lymphocyte (CTL) response against at least one T cell epitope, the method comprising administering to a mammal in need thereof:

- a compound provoking lymphocytopenia; and
- a molecule, with selective affinity for professional antigen presenting cells (APC), which comprises a foreign antigen that bears at least one said T cell epitope.

According to the present invention said T cell epitope may be a T cell epitope from an antigen derived from an infectious disease agent or a cellular malignancy, dysplasia, tumor or cancer.

According to the present invention the compound provoking lymphocytopenia and the molecule, with selective affinity for professional antigen presenting cells (APC), which comprises a foreign antigen that bears at least one said T cell epitope may be administered simultaneously, separately or successively to the patient, preferably when said compound and said molecule are administered successively to the patient, said compound provoking lymphocytopenia may be administered before said molecule, with selective affinity for professional antigen presenting cells (APC), which comprises a foreign antigen that bears at least one said T cell epitope.

According to the present invention, when the compound provoking lymphocytopenia and the molecule, with selective affinity for professional antigen presenting cells (APC), which comprises a foreign antigen that bears at least one said T cell epitope are administered simultaneously, said compound and said molecule may be administered in a same or in a separate composition.

In another embodiment, the present invention relates to a method for inducing a therapeutic immune response in a mammalian patient suffering from a chronic infectious disease, or of a cellular malignancy, dysplasia, tumor or cancer, which method comprises administering to a patient in need thereof:
  a composition comprising a compound provoking lymphocytopenia; and
  a composition comprising molecule, with selective affinity for professional antigen presenting cells (APC), which comprises a foreign antigen that bears at least one said T cell epitope that bears an antigen of respectively the infectious disease agent or of the cellular malignancy, the dysplasia, the tumor or the cancer.

According to the present invention, the composition comprising the compound provoking lymphocytopenia and the composition comprising the molecule, with selective affinity for professional antigen presenting cells (APC), which comprises a foreign antigen that bears at least one said T cell epitope may be administered simultaneously, separately or successively to the patient, preferably when said compound and said molecule are administered successively to the patient, said compound provoking lymphocytopenia is administered before said molecule, with selective affinity for professional antigen presenting cells (APC), which comprises a foreign antigen that bears at least one said T cell epitope.

According to the present invention, when the composition comprising the compound provoking lymphocytopenia and the composition comprising the molecule, with selective affinity for professional antigen presenting cells (APC), which comprises a foreign antigen that bears at least one said T cell epitope are administered simultaneously, said compositions may be administered in a same or in a separate composition.

According to the present invention said mammalian patient may be a human.

In another embodiment, the present invention relates to a pharmaceutical composition for eliciting in a mammal a specific cytotoxic T lymphocyte (CTL) response against at least one T cell epitope or for inducing a therapeutic immune response in a mammalian patient suffering from a chronic infectious disease, or of a cellular malignancy, dysplasia, tumor or cancer, wherein said composition comprises:
  a compound provoking lymphocytopenia;
  a molecule, with selective affinity for professional antigen presenting cells (APC), which is associated to said T cell epitope or which is associated to an antigen of respectively the infectious disease agent or of the cellular malignancy, the dysplasia, the tumor or the cancer; and
optionally, a pharmaceutical acceptable carrier.

In another embodiment, the present invention relates to a kit for eliciting in a mammal a specific cytotoxic T lymphocyte (CTL) response against at least one T cell epitope or for inducing a therapeutic immune response in a mammalian patient suffering from a chronic infectious disease, or of a cellular malignancy, dysplasia, tumor or cancer, wherein said kit comprises:

- a composition comprising a compound provoking lymphocytopenia; and
- a composition comprising molecule, with selective affinity for professional antigen presenting cells (APC), which comprises a foreign antigen that bears at least one said T cell epitope bearing an antigen of respectively the infectious disease agent or of the cellular malignancy, the dysplasia, the tumor or the cancer.

According to the present invention, the pharmaceutical composition or the kit may be a vaccine.

According to the present invention, the composition may be formulated for intramuscular, intravenous, intradermal, cutaneous, subcutaneous, intraperitoneal mucosal, or oral administration.

According to the present invention molecule, the molecule with selective affinity for professional antigen presenting cells (APC), which comprises a foreign antigen that bears at least one said T cell epitope consists of a molecule with selective affinity for professional antigen presenting cells (APC) that may be covalently coupled to said antigen bearing at least one T cell epitope.

According to the present invention, the molecule, with selective affinity for professional antigen presenting cells (APC) and said antigen bearing at least one T cell epitope may be polypeptides encoded by DNA sequences fused by recombinant DNA technology.

According to the present invention, the compound provoking lymphocytopenia may be a compound capable of provoking transient T cells depletion.

According to the present invention, the compound provoking lymphocytopenia may be selected from the group consisting of ATG and fludarabine.

According to the present invention, the molecule having selective affinity for professional antigen presenting cells may be selected from the group consisting of adenylate cyclase (CyaA), Heat Shock Protein (HSP) shigatoxin, and LAG-3.

In an embodiment, the invention concerns a method of use of the adenylate cyclase (CyaA) vector derived from *Bordetella pertussis*, whereby the CyaA vector shows improved performance as vaccine vector when used in combination with lympho-ablative compounds in comparison with vaccines that do not target professional antigen presenting cells.

In an embodiment, the invention concerns a pharmaceutical composition of matter consisting of an ingredient comprising an ATG and an ingredient comprising a CyaA that harbours foreign antigenic sequences. Said antigenic sequences can be derived from any infectious disease agent provoking chronic infection and from any abnormally dividing mammalian cell, dysplasia, tumour or cancer.

In an embodiment, the invention concerns a pharmaceutical composition of matter consisting of an ingredient comprising fludarabine and an ingredient comprising a CyaA that harbours foreign antigenic sequences. Said antigenic sequences can be derived from any infectious disease agent provoking chronic infection and from any abnormally dividing mammalian cell, dysplasia, tumour or cancer.

According to the present invention, said adenylate cyclase may be from *Bordetella pertussis* or said HSP is hsp65 is from *Mycobacterium bovis*, hsp 70, more preferably hsp 65 or said shigatoxin is from *Shigella dysenteriae*.

According to the present invention, said T cell epitope are selected from the group consisting of:

- T cell epitope from tumour antigen selected from the group consisting of carcino-embryonic antigen (CEA), particularly carrying the A3-B3 region, MAGE-A3, TERT, the E7 oncogene from the Human Papillomavirus (HPV) and P53; and T cell epitope from infectious agent selected from the group consisting of HPV, HIV, HBV, HCV, *Chlamydia trachomatis*, and *Mycobacterium tuberculosis*, In another embodiment, the present invention relates to a method for the prevention or for the treatment of a tumour, particularly a malignant tumour, in a mammal patient, wherein the tumour cells express a specific tumour associated-antigen, said tumour associated-antigen presenting a T cell epitope, said method comprising the administration to a patient in need thereof of a composition comprising:
- a compound provoking lymphocytopenia; and
- a molecule, with selective affinity for professional antigen presenting cells (APC), which comprises a foreign antigen that bears at least one said T cell epitope, which comprises said tumour associated-antigen specific of said tumour or said T cell epitope contained in said tumour associated antigen.

The present invention also relates to a method for the prevention or for the treatment of a tumour, particularly a malignant tumour, in a mammal patient, wherein the tumour cells express a specific tumour associated-antigen, said tumour associated-antigen presenting a T cell epitope, said method comprising the administration to a patient in need thereof of a composition comprising:
- a compound provoking lymphocytopenia; and
- a molecule, with selective affinity for professional antigen presenting cells (APC), which comprises a foreign antigen that bears at least one said T cell epitope, which comprises said tumour associated-antigen specific of said tumour or said T cell epitope contained in said tumour associated antigen.

In another embodiment, the present invention relates to a method for the prevention or for the treatment of an infection in a mammal patient, wherein the agent responsible of said infection expresses a specific antigen presenting a T cell epitope, said method comprising the administration to a patient in need thereof of a composition comprising:
- a compound provoking lymphocytopenia; and
- molecule, with selective affinity for professional antigen presenting cells (APC), which comprises a foreign antigen that bears at least one said T cell epitope that comprises said antigen specific of said agent responsible of said infection or at least one T cell epitope contained in said antigen.

In another embodiment, the present invention relates to a method for the prevention or for the treatment of a cancer in a mammal patient, particularly cancer of the respiratory or digestive tractus, wherein the tumour cells express the CEA, said method comprising the administration to a patient in need thereof of:
- a composition comprising the compound ATG provoking lymphocytopenia; and subsequently
- a composition comprising a recombinant adenylate cyclase carrying the A3-B3 region of CEA protein.

In another embodiment, the present invention relates to a method for the prevention or for the treatment of a cancer induced by a HPV in a mammal patient, wherein the tumour cells express the E7 oncogene of HPV, said method comprising the administration to a patient in need thereof of:
- a composition comprising a rabbit or horse polyclonal ATG provoking lymphocytopenia; and subsequently
- a composition comprising a recombinant adenylate cyclase carrying the E7 oncogene From HPV.

The present invention will be understood more clearly on reading the description of the experimental studies performed in the context of the research carried out by the applicant, which should not be interpreted as being limiting in nature.

An industrial application of the present invention may be an:

Improved adaptive immunotherapy of cancer targeted at malignant or neoplastic cells that specifically express the tumour antigens, preferentially CEA, E7, MAGE-A3, TERT and P53 polypeptide sequences that each independently are jointly inserted into the APC-targeting vaccine vector, preferentially recombinant protein vectors such as adenylate cyclase (CyaA) vector, Heat Shock protein vectors (Hsp65), shigatoxin, or recombinant protein vectors containing APC ligand sequences such as LAG-3.

Improved adaptive immunotherapy of latent or chronic infectious diseases targeted at infected cells of the patient that specifically express antigens of the infectious disease agent, preferentially of viruses and in particular HPV, HIV, HBV and HCV or of intra-cellular bacteria such as *Chlamydia trachomatis, Mycobacterium tuberculosis*, that are inserted into the APC-targeting vaccine vector, preferentially the CyaA vector, or heat shock protein (hsp), shigatoxin or recombinant protein vectors containing APC ligand sequences such as LAG-3. Improved vaccines comprising an APC-targeting vector such as CyaA, Hsp65, Hsp70, Shigatoxin, LAG-3, the antigenic sequences of choice derived from CEA, E7, MAGE-A3, TERT, P53, HPV, HIV, HBV, HCV, *Chlamydia trachomatis, Mycobacterium tuberculosis*, coupled or inserted into the vector and an immuno-depletory molecule such as fludarabine, ATG, whereby the immuno-depletory component is preferentially administered to the patient prior to the other components or concurrently but mixed ex temporanis.

EXAMPLES

The following examples 1 and 2 are similar, except the fact that in Example 2, administration of the molecule having selective affinity for APCs is made in the presence of a CpG adjuvant.

1. Example 1

This example concerns the use in a murine model of lymphoablative regimen prior to *B. pertussis* adenylate cyclase-based prime boost immunotherapy. Immunosuppression, mediated by low doses of rabbit anti-thymocytes globulins or fludarabine, was transient and resulted in the induction of higher frequencies of antigen-specific T cells upon immunotherapeutic treatment. This correlated with a higher ability of mice to control/reject the growth of aggressive tumor cells expressing the antigen of interest. This approach presents new possibilities to improve the therapeutic potential of this vector in cancer or other infectious diseases.

The CarcinoEmbryonic Antigen is a tumor associated antigen that is over expressed in many malignancies particularly from the digestive tract and the lungs. By inserting sub-fragments of CEA in the catalytic domain of CyaA, a construct that demonstrated immunogenicity in C57/BL6 mice has been generated. ATG- and fludarabine-mediated lymphodepletion resulted in marked increase in the number of CEA-specific T lymphocytes upon prime-boost immunization with CyaA-CEAA3B3. This phenomenon appeared to be specific to vectorization of CEA by CyaA as it was not observed for CD8+ lymphocytes upon vaccination with CEAA3B3 protein formulated with the CpG adjuvant. From experiments evaluating the effect of adjuvants on vaccines based on the adenylate cyclase vector, the inventors have shown that the frequency of epitope-specific T cell responses can be strongly enhanced if the CyaA-based vaccine carrying said epitope, is supplemented with any of following adjuvants: lipid A (monophosphoryl-A), poly ICLC or CpG, which are ligands of the respective Toll-like receptor classes 3, 4 and 9 (data not shown).

ATG preparations described in this example are polyclonal rabbit IgGs prepared upon immunization with lymphocytes or thymocytes. They have been used in human transplantation since the late 1960s (23) for the following indications: prevention (induction therapy) and treatment of acute rejection of organ allografts, including steroid resistant rejection, treatment of graft-versus-host disease after bone marrow transplantation (24), therapy of a plastic anemia (25), and conditioning of recipients of bone marrow from unrelated HLA-matched (26) or haploidentical related donors (27).

1.1 Materials and Methods 1.1.1 Mice, cell lines

Specific pathogen-free 6- to 10-week-old female C57BL/6 mice were obtained from CER Janvier (Le Gesnet St-Isle, France). Experiments involving animals were conducted according to the institutional guidelines for animal care. Immunosuppressive treatments were administred ip, tumor cells, sc and immunization, iv (retro-orbitally) and id in the ear dermis. Blood sampling was performed by tail bleeding. Splenectomies and lymph node sampling were performed on sacrificed animals (CO2). Axillary, mesenteric and inguineal lymph nodes were sampled and pooled for phenotyping analysis.

B16F0 cells expressing CEA protein were obtained upon co-transduction of pIRES-EPI plasmid encoding CEA and GFP with rMLV plasmid (Vectalys). B16F0CEA-GFP cells were maintained in RPMI 1640 with GlutaMAX supplemented with 10% heat inactivated FCS, 100 units/mL penicillin, 100 µg/mL streptomycin, and $5 \times 10^{-5}$ mol/L 2-mercaptoethanol (Life Technologies).

1.1.2 Cell Numeration and Phenotyping.

Blood, lymph node cells and splenocytes were processed according to previously described methods (28, 29) for numeration and flow cytometry assited phenotyping. Blood lymphocytes were counted using Türk blue.

1.1.3 Preparation of Anti Mouse Thymocyte Globulins in Rabbit.

Mouse ATG were prepared by injecting a rabbit sc with $5 \times 10^8$ thymocytes sampled on 6-weeks old C57BL/6 mice. This immunization was boosted 14 days later with an iv injection of identical material. Seven days later the animal was bled and serum IgG were purified on immobilized protein G column (Pierce). Purity was controlled by SDS PAGE analysis and quantity was estimated by the Bradford method with known concentration rabbit IgG as standards. Rabbit ATG was used at a concentration of 20 mg/kg with a single injection. As a control, normal rabbit serum was used.

1.1.4 Reagents, Peptides and Oligonucleotides.

Fludarabine (Sigma) was used at a concentration of 200 mg/kg/day for 6 consecutive days. Monoclonal antibodies: anti-CD4-APC, anti-CD8-PerCP, anti-B220-FITC and anti-IFN-γ-FITC were obtained from BD Biosciences.

A pepscan of 15-mers overlapping by 11 amino acids and covering the A3 and B3 domain of the CEA protein was designed and obtained from Mimotope™ (Australia). It was diluted in DMSO and used at a final concentration of 1 µg/ml. CpG ODN 1826 was purchased from Proligo (Paris, France), it was used at a final dose of 10 µg per injection. Said CpG is of sequence SEQ ID NO16, wherein the bases are phosphorothioate (nuclease resistant).

1.1.5 Molecular cloning of Recombinant *B. pertussis* CyaA Carrying CEA A3 and B3 domains. Production and purification of recombinant CyaA-CEAA3B3. Recombinant adenylate cyclase used in this article were expressed in *Escherichia coli* by using derivatives of plasmid pkTRAC-HPV16E7A30-42 which codes for an enzymatically inactive CyaA (21).

CyaA-CEAA3B3 was constructed in two steps. A first DNA fragment encoding amino acid residues 492-557 of CEA was PCR-amplified using a synthetic CEA gene (Sequentia) and primers CEA1 (SEQ ID NO1: 5'-accatcac-cgtctctgcg-3') and CEA2 (SEQ ID NO2: 5'-gggcactagtggtca-gggtacggttgcc-3'). A second DNA fragment encoding amino acids residues 629-687 of CEA was PCR-amplified using CEA synthetic gene and primers CEA3 (SEQ ID NO3: 5'-gggcaccggtaatggtatcccgcagcaacac-3') and CEA4 (SEQ. ID NO4: 5'-cgcagagacggtgatggtgttaacggcacccgcagacagacc-3'). These two DNA fragments (which partly overlap) were purified and combined with primers CEA2 and CEA3 in a third PCR to amplify a 395-bp-long DNA fragment. This fragment was digested by NheI and KpnI and inserted between the corresponding sites of pkTRAC-HPV16E7Δ30-42 to yield plasmid pkTRAC-CEAB3. Then, a DNA fragment encoding the amino acid residues 545 to 647 of CEA was PCR-amplified using the synthetic CEA gene and primers CEA5 (SEQ ID NO5: 5'-gggcgctagccgtctgcagctgtc-caatg-3') and CEA6 (SEQ ID NO6: 5'-cccgggtacccggcgt-gattttggcgata-3'). The purified PCR fragment was digested by AgeI and SpeI, and ligated into plasmid pkTRAC-CEAB3 digested by the same restriction enzymes.

CyaAΔ-CEAA3B3 was constructed in three steps. First, a DNA fragment corresponding to CyaA amino acid sequence 1149 to 1230 was PCR-amplified using pTRACE5 (30) as DNA and primers CyaAΔ1 (SEQ ID NO9: 5'-gggc-gagctctggggccacgat-3') and CyaAΔ2 (SEQ ID NO10: 5'-act-agtgcctcgatcccgaagccg-3'). A second DNA fragment encoding amino acid residues 1300 to 1356 of CyaA was PCR-amplified with the same plasmid DNA and primers CyaAΔ3 (SEQ ID NO11: 5'-actagtcatgctgtatggcgacgc-3') and CyaAΔ4 (SEQ ID NO12: 5'-cccggcatgcgcgccggtctgg-3'). These partly overlapping DNA fragments were purified and combined with primers CyaAΔ1 and CyaAΔ4 in a third PCR to amplify a 427-bp-long DNA fragment. This fragment was digested by SacI and SphI and ligated into plasmid pkTRACC-CEAA3B3 digested by the same restriction enzymes. The resulting plasmid pKTRACΔ-CEAA3B3, encoded a CyaA devoid of binding to the CD11b molecule (31).

All constructions were verified by DNA sequencing (Genome Express). Recombinant CyaAs were produced in the *E. coli* strain BLR (Novagen) as previously described (21). The recombinant proteins were purified to homogeneity from inclusion bodies by a two-step procedure that includes DEAE-Sepharose and phenyl-Sepharose chromatography. An additional washing step with 60% isopropanol was done (21) in order to eliminate most of the contaminating lipopolysaccharides. Purified recombinant proteins were analyzed by Coomassie blue-stained SDS-PAGE. Protein concentrations were determined spectrophotometrically from the absorption at 280 nm using a molecular extinction coefficient of 142,000 mol/L 1 cm 1.

1.1.6 Molecular Cloning of Recombinant CEA A3 and B3 Domains.

Production and Purification of Recombinant CEAA3B3 Protein.

The E. coli-optimized cDNA coding for CEAA3B3 protein was subcloned into pTriEx-1.1 hygro vector (Novagen) between the NotI and XhoI restrictions sites after PCR amplification with primers CEA7 (SEQ ID NO7: 5'-gcggccgcaccatcaccgtctctgcg-3') and CEA8 (SEQ ID NO8: 5'-cccgctcgagggcacccgcagacagacc-3'). The resulting plasmid was then transformed into the E. coli strain BL21λDE3 (Novagen). The His-Tag-CEAA3B3 protein was expressed upon induction with 0.5 mmol isopropyl-h-D-thiogalactopyranoside (Euromedex) and purified on Ni-NTA agarose (Qiagen). Isopropanol washes were used in order to remove lipopolysaccharide contamination.

1.1.7 Intracellular Cytokine Staining

Splenocytes were stimulated in vitro for 36 hours in the presence (or absence) of the complete CEAA3B3 pepscan pool. Brefeldin-A was added after the first hour of incubation. Cells were permeabilized using FACSPerm2 (BD Biosciences) and stained with monoclonal antibodies anti-CD4-APC, anti-CD8-PerCP and anti-IFN-γ-FITC. The cells were analysed using a FACScalibur® flow cytometer (BD Biosciences) and the percentage of cytokine secreting cells was determined after first gating on CD4+ or CD8+ cells.

1.2 Results 1.2.1 SDS PAGE Analysis of Purified Recombinant Proteins.

Figure 1:
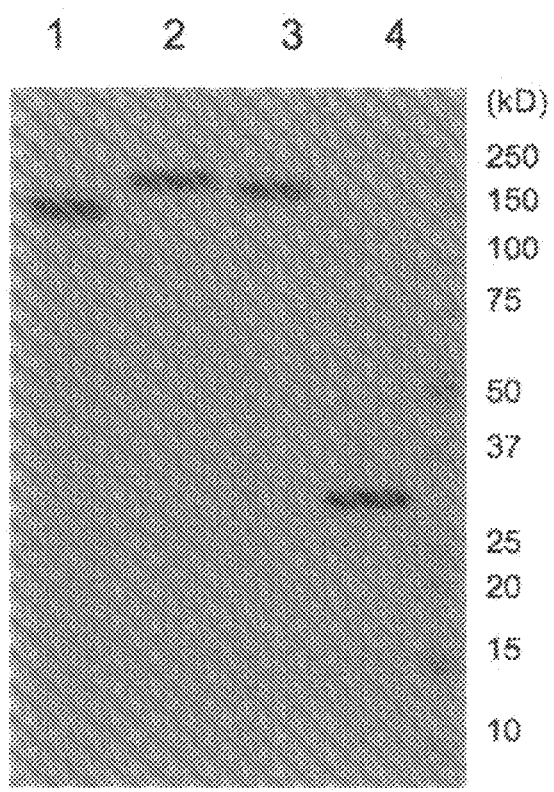
FIG. 1 (example 1): SDS-PAGE analysis of the CEA recombinant proteins.

To study the ability of the CyaA vector to induce CEA-specific T cell responses, three different recombinant molecules containing A3 and B3 domains of the CEA molecule have been constructed. This region of CEA has been shown to contain many human CTL and helper epitopes (32) as well as the two H-2b restricted epitopes described to date (33, 34). To allow in vitro and in vivo assays, the constructs were produced in E. coli and purified to homogeneity (FIG. 1). A lipopolysaccharide elimination procedure was introduced in the purification protocol (21) to obtain recombinant proteins containing <300 units of endotoxin per mg (data not shown).

1.2.2 Moderate Amplification of the Cellular Immune Response Induced by Prime-Boost Immunization with Recombinant CEA Proteins.

Previous studies have shown that recombinant CyaA carrying antigens of interest are able to induce cellular T cell responses of the Th1 type upon different route of injection (21, 35). The inventors investigated whether combining different routes of injection through a prime boost approach could increase the magnitude of the cellular immune response. As shown in FIG. 2, the frequencies of CEA-specific CD4+ and CD8+ splenocytes secreting IFN-γ were already fairly high after one single intra-venous (iv) administration of 50 μg of CEA recombinant proteins. Of note, CyaAΔ-CEAA3B3 lacking the interaction domain with CD11b substantially lost its vector abilities. In contrast, the CEAA3B3 protein formulated with the adjuvant (CpG) was able to mount a cellular immune response of the Th1 type. CEA-specific IL-5 CD4+ T cells were detected in significant amount only among splenocytes from CyaAΔ-CEAA3B3-immunized mice (data not shown).

The immunization experiments described above were repeated but with altered administration method: A prime vaccination was made iv, followed respectively 7 and 14 days later by an id injection of 10 μg of material in the ear dermis (prime-double boost vaccination). The first boost resulted in a moderate increase of the frequency of CEA specific T cells in mice vaccinated with CyaA-CEAA3B3 or CEAA3B3+ CpG. The second boost did not have any significant effect on this frequency parameter (FIG. 2).

Bearing in mind that a key objective of cell-based tumor immunotherapy is to mount a strong and specific T cell response against defined antigens, in a situation whereby the patient is often immuno-suppressed due to other treatments (chemo- and radio-therapy), it appeared important to evaluate vaccination conditions under lymphodepletory circumstances. The inventors have therefore included immunosuppressive drugs with moderate and or adjustable T cell depleting properties in the experimental design.

1.2.3 Lymphocyte Depletion in Peripheral Blood Induced by Immunosuppressive treatment.

Rabbit ATG are polyclonal IgGs that have been used in solid organ transplantation for quite a long time now. Studies performed in monkeys revealed that dose-dependent lymphocyte depletion is achievable with rabbit ATG (28). Fludarabine is a fluorinated analog of adenine that is commonly used to treat chronic lymphocytic leukemia (39). Fludarabine causes lymphopenia, depleting T lymphocytes more markedly than B lymphocytes (40).

The evolution of blood lymphocytes sub-populations upon immunosuppressive treatment by rabbit ATG or fludarabine has been analysed. Previous studies allowed the inventors to achieve a mild lymphodepletion in C57BL/6 mice with a single ip injection of 20 mg/kg body weight (data not shown). In these conditions, they observed a two-fold decrease of the number of circulating lymphocytes 2 hours after ATG injection (FIG. 3). These values slowly returned close to normal levels upon a period of eight days. A quasi complete disappearance of CD4+ and CD8+ T lymphocytes was observed 2 hours after ATG injection, that was paralleled by a relative increase in the percentage of B lymphocytes. Reconstitution of the T lymphocyte compartment started thereafter, and close to normal values were recovered within 15 days. From the literature (41, 42) a fludarabine-based regimen of 200 mg/kg/day ip for 6 days appeared necessary to induce also a mild lymphodepletion in mice. In these conditions, depletion of the peripheral blood T lymphocyte compartment appeared less markedly pronounced than with ATG with returning to normal level after then end of chemotherapeutic treatment.

1.2.4 Lymphocyte Depletion in Lymphoid Organs Induced by Immunosuppressive Treatment.

The blood compartment represents only 1 to 2% on the total body lymphoid mass. Lymphocyte depletion by phenotyping for T and B cells, spleen and lymph nodes 10 days after onset of immunosuppression has been monitored. Similarly to the situation in the blood compartment, ATG- and fludarabine-based immunosuppressive therapies induced a depletion of the T lymphocyte pool in lymphoid organs (Table 1).

Table 1 shows peripheral lymphoid organ depletion induced by a single ATG injection. Peripheral lymphoid organs were sampled 10 days after onset of immunosuppressive treatment administration. Values presented are the percentages of CD4, CD8 and B220 cells observed in the spleen and lymph nodes.

TABLE 1

|      |            | Spleen | Lymph nodes |
|------|------------|--------|-------------|
| CD4+ | PBS        | 25.6   | 48.1        |
|      | NRS        | 26.7   | 47.6        |
|      | ATG        | 14.6   | 28.5        |
|      | Fludarabine| 21.9   | 37.8        |

TABLE 1-continued

|      |            | Spleen | Lymph nodes |
|------|------------|--------|-------------|
| CD8+ | PBS        | 10.9   | 26.3        |
|      | NRS        | 11.3   | 27.4        |
|      | ATG        | 3.9    | 13.9        |
|      | Fludarabine| 5.3    | 20.8        |
| B220+| PBS        | 49.2   | 19.9        |
|      | NRS        | 48.6   | 19.4        |
|      | ATG        | 59.6   | 47.8        |
|      | Fludarabine| 54.3   | 32.4        |

The effect was more pronounced with ATG than fludarabine. It was paralleled by a relative increase of the B lymphocyte pool.

In summary, under the immunosuppressive conditions used in their study, a marked but moderate and transient decrease of the T lymphocytes compartment has been observed.

1.2.5 Increased Magnitude of CEA-Specific Th1 Response as a Result of Immunosuppression and Prime-Boost Immunization.

It has been next sought to determine whether lymphodepletion performed in the conditions described above could allow to increase the magnitude of CEA-specific T cell response in their immunization model. Ten days prior to prime-boost immunization (50 μg iv and 10 μg id seven days later), animals were treated with ATG or fludarabine as described above. As compared to controls, the magnitude of CEA-specific cellular immune response was markedly enhanced in ATG and fludarabine treated animals immunized with CyaA-CEAA3B3. Indeed, FIG. 4 shows that the frequency of CEA-specific CD4+ and CD8+ T cells secreting IFN-γ was doubled in animals that received prior lymphoablative treatment. Such an effect was not observed in animals immunized with CyaAΔ-CEAA3B3, thus highlighting the importance of CD11b targeting for CyaA-based therapy. Of note, prior lymphodepletion resulted in a marked increased frequency of CEA-specific CD4+ T cells secreting IFN-γ upon CEAA3B3+ CpG immunization, but this effect was not seen for CEA-specific CD8+ T cells.

1.2.6 Increased Survival Median Following CyaA-CEAA3B3 Prime Boost Immunization as a Result or Prior Lymphoablation.

Figure 5A:
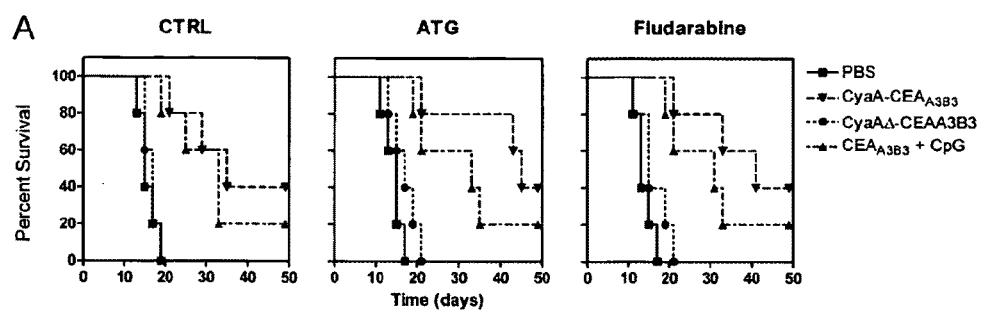
Figure 5B:
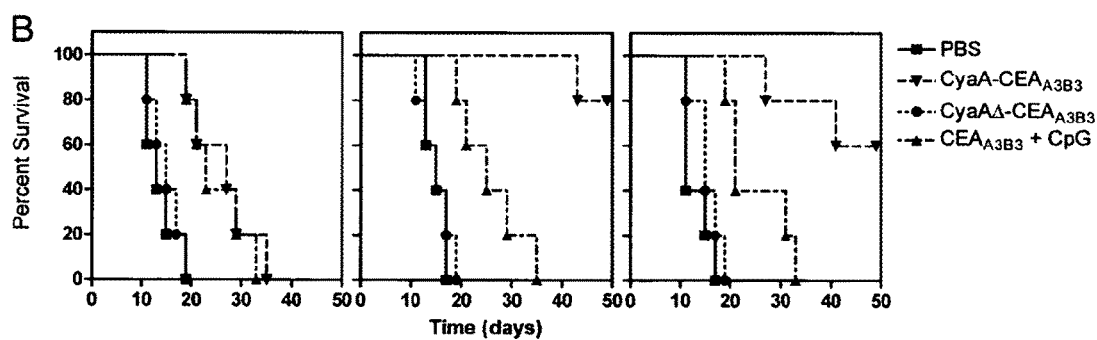

Next, the relevance of this observation has been tested in a tumor rejection model. The inventors established B16 cell lines stably expressing CEA protein. Upon injection of $2 \times 10^4$ tumor cells, all mock- and CyaAΔ-CEAA3B3-treated animals developed tumors and became moribund, necessitating euthanasia (FIG. 5). In these conditions, the survival medians of the animals were 15 and 17 days respectively. In contrast, animals immunized 3 days after tumor injection, with CyaA-CEAA3B3 and CEAA3B3+ CpG, had enhanced survival medians (35 and 33 days, respectively). A small proportion of these animals were tumor free 50 days after B16F0CEA-GFP cells injection (FIG. 5A). Upon lymphodepletion with ATG or fludarabine, the survival median of CyaA-CEAA3B3-treated mice was further enhanced to 45 and 41 days, respectively, whereas that of CEAA3B3+ CpG-immunized animals remained unchanged. The proportion of animals remaining tumor free was not modified. As shown in FIG. 5B, animals in which tumors had been allowed to grow 5 days prior to therapeutic immunization with CyaA-CEAA3B3, showed a drastic enhanced survival upon lymphodepletion as compared to controls. Indeed, in this setting, the survival medians of CyaA-CEAA3B3- and CEAA3B3+ CpG treated mice were decreased to 27 and 23 days, respectively, with no animals remaining tumor free at day 50. Lymphodepletion had no effect on the survival medians of CEAA3B3+ CpG-immunized mice. In contrast, the survival of ATG of fludarabine treated animals was drastically enhanced by CyaA-CEAA3B3 immunisation so that 50 days tumor-free survival increased to 80% and 60% respectively.

1.3 Discussion

Many issues hamper the translation of pre-clinical results to the clinic in the field of cell-based adoptive tumor immunotherapy. One of them is the magnitude of the induced adoptive response to the tumor associated antigen of interest. Indeed, in humans the growth and efficacy of antigen specific T cells are limited by multiple factors in the context of tumor development. These include, lack of induction of T cell clones with high affinity to the TAA, negative signals from regulatory cells, tumor stroma and homeostatic T cell regulation. In murine models of adoptive T cell transfer therapies, lymphodepletion has been shown to increase engraftment and persistence of transferred cells (43-46). Such strategies have been quite successfully translated to the clinic most recently (36-38). Using a powerful tool for inducing specific CD8+ and CD4+ T cell responses, the adenylate cyclase from *B. pertussis*, it has been sought to determine the impact of lymphodepletion on active immunization aimed at inducing specific T cell responses. It has been chose to target the Carcino-Embryonnic Antigen because of its overexpression in numerous types of cancer.

The lack of immunogenicity of CyaAΔ-CEAA3B3 highlighted the importance of CD11b targeting in the ability of CyaA to induce specific T cells responses. As demonstrated in a previous study (21), CyaA-CEAA3B3 turned out to be as efficient as CEAA3B3+ CpG in terms of immunogenicity (FIG. 2) and tumor immunotherapy (FIG. 5).

The efficiency of CyaA as a vector tool has been shown to be unaffected by prior immunity (20, 21), thus allowing homologous prime-boost strategies. By using two different routes of injection, the inventors were able to increase the scale of CEA-specific immune response albeit to moderate levels. It has not been possible to further amplify the cellular immune response by a second id boost. The inventors then hypothesized that a transient mild lymphodepletion would create the necessary space to allow specific T cell clones to further amplify. They focused on products extensively used in humans that have been shown to preferentially deplete T lymphocytes. Patterns of lymphodepletion obtained upon ATG treatment were coherent with those observed in a non human primate model (28). The overall level of lymphodepletion obtained with fludarabine was inferior to that of ATG but it is known that fludarabine works better in association with cyclophosphamide (42).

With prior lymphodepletion, it has been possible to almost double the frequency of CEA-specific T lymphocytes. Whether this due to the disruption of homeostatic T cell regulation or the destruction of regulatory T cells remains to be investigated. It cannot be exclude that lymphodepletion induces higher levels of cytokines to be available for remaining activated lymphocytes so as to facilitate their development and amplification.

Lymphodepletion did not increase the frequency of CEA-specific CD8+ T cells upon CEAA3B3+ CpG immunization in contrast to CyaA-CEAA3B3 immunization. This highlights the importance of APC targeting in the phenomenon described here. CyaA vector targets DC through its property to translocate its catalytic domain into the cytosol of CD11b+ antigen presenting cells (17, 18). Of interest, a similar result of increased frequency of CEA- specific CD8+ lymphocytes following lymphodepletion with another system, the hsp65 protein of *M. bovis* fused to CEAA3B3 (data not shown) has been observed. Nevertheless, it cannot be excluded that their conditions of experiment, inflammatory conditions induced by CpG inhibit the formation of a sufficient pool of memory T cells for boosting as it has been shown in another model (47).

The level of CEA-specific T lymphocytes was linked to the ability of animals to survive to tumor challenge mediated by B16F0CEA-GFP cells suggesting a correlation between the number of CEA-specific lymphocytes and the ability for the mice to control and/or reject CEA expressing tumor cells. The effect of prior lymphodepletion on the efficiency of CyaA-CEAA3B3 prime boost immunization was more pronounced in the D+5 than the D+3 therapeutic setting. This observation may reflect the necessity of a precisely controlled timing between lymphodepletion and lymphostimulation to obtain a maximal effect as lymphoablative drugs may have effects lasting after their disappearance from the organism. In this respect, ATG counterpart for human use has been shown to down-modulate lymphocyte surface receptors, which renders them poorly responsive to antigen-induced proliferation (28). It can not be excluded this phenomenon to be involved in the apparent lack of effect in the D+3 therapeutic setting as the delay between lymphodepletion and immunization was only 8 days in this case.

This study demonstrates that CyaA-based active cell-based immunotherapy is compatible with lymphodepletion mediated by ATG or fludarabine. In such a context, prime-boost immunization by two different mutes of injection (iv, id) markedly increased the frequency of CEA-specific T helper and most importantly, CEA-specific cytotoxic T lymphocytes. This increased frequency of CEA-specific cytotoxic T lymphocytes correlated with a better ability to control and/or reject CEA expressing tumor cells. From the results presented, it is preferable to use a vector that targets antigen presenting cells such as CyaA or hsp65 to obtain such a result. Indeed, CyaAΔ which is devoid of CD11b binding has lost its ability to induce CEA-specific T cells. Furthermore, CEA-specific CD8+T cells response induced by CEAA3B3 formulated with CpG adjuvant, was not further amplified in the lymphodepletion conditions used here.

2. Example 2

2.1 Materials and Methods

2.1.1 Mice, Cell Lines

Specific pathogen-free 6- to 10-week-old female C57BL/6 mice were obtained from CER Janvier (Le Gesnet St-Isle, France). Experiments involving animals were conducted according to the institutional guidelines for animal care. Immunosuppressive treatments were administred ip, tumor cells, sc and immunization, iv (retro-orbitally) and id in the ear dermis. Blood sampling was performed by tail bleeding. Splenectomies and lymph node sampling were performed on sacrificed animals ($CO_2$). Maxillary lymph nodes were sampled and pooled for phenotyping analysis.

MC32aCEA cells expressing CEA protein were obtained from Pr. W. Zimermann (LTI, Munich). These cells are derived from the MC38 murine colon adenocarcinoma (48). Cells were maintained in RPMI 1640 with GlutaMAX supplemented with 10% heat inactivated FCS, 100 units/mL penicillin, 100 μg/mL streptomycin, and $5\times10^{-5}$ mol/L 2-mercaptoethanol in presence of 0.3 mg/ml G418 (Life Technologies).

2.1.2 Cell Numeration and Phenotyping.

Blood, lymph node cells and splenocytes were processed according to previously described methods (28, 29) for numeration and flow cytometry assisted phenotyping. Blood lymphocytes were counted using Trypan blue.

2.1.3 Preparation of Anti Mouse Thymocyte Globulins in Rabbit.

Mouse ATG were prepared by injecting a rabbit sc with $5\times10^8$ thymocytes sampled on 6-weeks old C57BL/6 mice. This immunization was boosted 14 days later with an iv injection of identical material. Seven days later the animal was bled and serum IgG were purified on immobilized protein G column (Pierce). Purity was controlled by SDS PAGE analysis and quantity was estimated by the Bradford method with known concentration rabbit IgG as standards. Rabbit ATG was used at a concentration of 20 mg/kg with a single injection. As a control, normal rabbit serum was used.

2.1.4 Reagents, Peptides and Oligonucleotides.

Fludarabine (Sigma) was used at a concentration of 100 mg/kg/day for 6 days. Monoclonal antibodies: anti-CD4-APC, anti-CD8-PerCP, anti-B220-FITC and anti-CD49d (Pan NK)-PE were obtained from BD Biosciences.

A pepscan of 15-mers overlapping by 11 amino acids and covering the A3 and B3 domain of the CEA protein was designed and obtained from Mimotope™ (Australia). It was diluted in DMSO and used at a final concentration of 1 μg/ml CpG ODN 1826 was purchased from Sigma. Said CpG is of sequence SEQ ID NO16, wherein the bases are phosphorothioate (nuclease resistant).

2.1.5 Molecular Cloning of Recombinant *B. pertussis* CyaA Carrying CEA A3 and B3 Domains. Production and Purification of Recombinant CyaA.

Recombinant adenylate cyclase used in this article were expressed in *Escherichia coil* by using derivatives of plasmid pkTRAC-HPV16E7$_{\Delta30-42}$ which codes for an enzymatically inactive CyaA (21).

CyaA-CEA$_{A3B3}$ was constructed in two steps. A first DNA fragment encoding amino acid residues 492-557 of CEA was PCR-amplified using a synthetic CEA gene (Sequentia) and primers CEA1 (SEQ ID NO1: 5'-accatcaccgtctctgcg-3') and CEA2 (SEQ ID NO2: 5'-gggcactagtggtcagggtacggttgcc-3'). A second DNA fragment encoding amino acids residues 629-687 of CEA was PCR-amplified using CEA synthetic gene and primers CEA3 (SEQ ID NO3: 5'-gggcaccggtaatggtatcccgcagcaacac-3') and CEA4 (SEQ ID NO4: 5'-cgcagagacggtgatggtgttaacggcacccgcagacagacc-3'). These two DNA fragments (which partly overlap) were purified and combined with primers CEA2 and CEA3 in a third PCR to amplify a 395-bp-long DNA fragment. This fragment was digested by NheI and KpnI and inserted between the corresponding sites of pkTRAC-HPV16E7$_{\Delta30-42}$ to yield plasmid pkTRAC-CEA$_{B3}$. Then, a DNA fragment encoding the amino acid residues 545 to 647 of CEA was PCR-amplified using the synthetic CEA gene and primers CEA5 (SEQ ID NO5: 5'-gggcgctagccgtctgcagctgtccaatg-3') and CEA6 (SEQ ID NO6: 5'-cccgggtacccggcgtgattttggcgata-3'). The purified PCR fragment was digested by AgeI and SpeI, and ligated into plasmid pkTRAC-CEA$_{B3}$ digested by the same restriction enzymes.

CyaAΔ-CEA$_{A3B3}$ was constructed in two steps. First, a DNA fragment corresponding to CyaA amino acid sequence 1149 to 1356 (SEQ ID NO13: 5'-caac-gagctctggggccacgatggcaacgacacgatacgcggccggggcggcgac-gacatcctgcgcggcggcctggg cctggacacgctgtatggcg-aggacggcaacgacatcttcctgcaggacgacgagaccgtcagcgatgacatc-gacggcg gcgcggggctggacaccgtcgactactc-cgccatgatccatccaggcaggatcgttgcgccgcatgaatacggcttcggga tcgaggccatgctgtatggcgacgccggcaacgacaccctctacgggggct-gggcgacgatacccttgaaggcggcgc gggcaacgattggttcggcc-agacgcaggcgcgcgagcatgacgtgctgcgcggcggagatggggtggatac-cgtcgatt acagccagaccggcgcgcatgccggcattgccgc-3') lacking nucleic acids corresponding to sequence 1230 to 1300 was synthetized (Genecust, France). Second, this fragment was digested by SacI and SphI and ligated into plasmid pkTRAC-CEA$_{A3B3}$ digested by the same restriction enzymes. The resulting plasmid pKTRACΔ-CEA$_{A3B3}$, encoded a CyaA devoid of binding to the CD11b molecule (31).

All constructions were verified by DNA sequencing (Ge-nome Express). Recombinant CyaAs were produced in the *E. coli* strain BLR (Novagen) as previously described (21). The recombinant proteins were purified to homogeneity from inclusion bodies by a two-step procedure that includes DEAE-Sepharose and phenyl-Sepharose chromatography. An additional washing step with 60% isopropanol was done (21) in order to eliminate most of the contaminating lipopo-lysaccharides. Purified recombinant proteins were analyzed by Coomassie blue-stained SDS-PAGE. Protein concentra-tions were determined spectrophotometrically from the absorption at 280 nm using a molecular extinction coeffi-cient of 142,000 mol/L 1 cm1.

2.1.6 Molecular Cloning of Recombinant CEA. Produc-tion and Purification of Recombinant CEA Protein.

The *E. coli*-optimized cDNA coding for CEA protein was subcloned into plvex 2.4b Nde vector (Roche) between the NcoI and XhoI restrictions sites after PCR amplification with primers CEA7 (SEQ ID NO14: 5'-aatctcgaggatcagcg-caacaccaacca-3') and CEA8 (SEQ ID NO15: 5'-atatccatg-gagtctccgtctgcc-3'). The resulting plasmid was then trans-formed into the *E. coli* strain BL21λDE3 (Novagen). The His-Tag-CEA protein was expressed upon induction with 1 mmol isopropyl-h-D-thiogalactopyranoside (Euromedex) and purified on Ni-NTA agarose (Qiagen). Endotrap resin (Profos, Germany) was used in order to remove lipopoly-saccharide contamination.

2.1.7 γ-IFN ELISpot Assay

Multiscreen filtration plates (96 wells; Millipore, France) were coated with 4 µg/ml of rat anti-mouse gamma inter-feron (IFN-γ) antibody (clone R4-6A2; PharMingen, San Diego, Calif.), overnight at room temperature. Spleen cells from immunized mice were added to the wells and incubated for 20 h with or without CEA pepscan at 1 µg/ml. After extensive washes, the plates were revealed by incubation with 5 µg/ml of biotinylated rat anti-mouse IFN-γ antibody (clone XMG 1.2; PharMingen) followed by incubation with streptavidin-alkaline phosphatase (PharMingen). Finally, spots were revealed using BCIP/NBT as substrate. The number of γ-IFN producing cells was determined by count-ing the number of spot-forming colonies (SFC) in each well (C.T.L., Germany), and the results were expressed as num-ber of SFC per 1×10$^6$ splenocytes (20).

2.2 Results 2.2.1 SDS PAGE Analysis of Purified Recombinant Pro-teins.

To study the ability of the CyaA vector to induce CEA-specific T cell responses, the Inventors constructed two different recombinant molecules containing sub-fragments of the CEA molecule: the A3 and B3 domains. This region of CEA has been shown to contain many human CTL and helper epitopes (32). As a control, they used a histidine-tagged full length CEA protein encompassing all the pos-sible epitopes. To allow in vitro and in vivo assays, the constructs were produced in *E. coli* and purified to homo-geneity (FIG. 6). A lipopolysaccharide elimination proce-dure was introduced in the purification protocol (21) to obtain recombinant proteins containing <300 units of endo-toxin per mg (data not shown).

2.2.2 Moderate Amplification of the Cellular Immune Response Induced by Prime-Boost Immunization with Recombinant CEA Proteins.

Previous studies have shown that recombinant CyaA carrying antigens of interest are able to induce cellular T cell responses of the Th1 type upon different route of injection (21, 35). The Inventors investigated whether combining different routes of injection through a prime boost approach could increase the magnitude of the cellular immune response. As shown in FIG. 7, the frequency of CEA-specific CD8+ splenocytes secreting γ-IFN were already fair after one single iv administration of 50 µg of CEA recom-binant proteins. In contrast, neither CyaAΔ-CEA$_{A3B3}$ nor His-tag-CEA protein formulated with an adjuvant such as CpG, were able to mount a cellular immune response characterized by γ-IFN secretion.

The Inventors repeated these experiments with a different administration approach: A prime vaccination was made iv as above, followed respectively 7 and 14 days later by an id injection of 10 µg of material in the ear dermis (prime-double boost vaccination). Adjuvant was included in the respective vaccination shots; the first boost resulted in an increase of the frequency of CEA specific T cells in mice vaccinated with CyaA-CEA$_{A3B3}$+CpG. The second boost injection again did not have significant effect on this fre-quency parameter (FIG. 7).

2.2.3 Lymphocyte Depletion in Peripheral Blood Induced by Immunosuppressive treatment.

Fludarabine is a fluorinated analog of adenine that is commonly used to treat chronic lymphocytic leukemia (39). Fludarabine causes lymphopenia, depleting T lymphocytes more markedly than B lymphocytes (40). Rabbit ATG are polyclonal IgGs that have been used in solid organ trans-plantation for quite a long time now. Studies performed in monkeys revealed that dose-dependent lymphocyte deple-tion was achievable with this therapeutic (28).

The Inventors analyzed the evolution of blood lympho-cytes sub-populations upon immunosuppressive treatment by Fludarabine or rabbit ATG. Fludarabine at 100 mg/kg/day ip for 6 days (41, 42) appeared to have a depleting effect restricted to T cells. It was transient as values returned to control groups within 7 days after onset of treatment. Rabbit ATG at 20 mg/kg as a single ip injection induced an important decrease of the number of circulating CD4+ and CD8+ lymphocytes as soon as 2 hours after ATG injection (FIG. 8). This depleting effect was maximal between 2 and 4 days post injection. Afterwards, CD4+ and CD8+ lym-phocytes counts started to increase without reaching normal values. CD8+ T lymphocytes were 10 times more depleted than CD4+ T cells. NK cells were also depleted by ATG treatment in a proportion somewhat comparable to that of CD4+ cells. In contrast, the number of B cells was not affected by ATG treatment.

2.2.4 Lymphocyte Depletion in Lymphoid Organs Induced by Immunosuppressive Treatment.

The blood compartment represents only 1 to 2% on the total body lymphoid mass. The Inventors therefore monitored lymphocyte depletion by phenotyping for T and B cells, spleen and lymph nodes 14 days after onset of immunosuppression. Compared to controls (PBS and NRS) Fludarabine- and ATG-based immunosuppressive therapies induced modifications of lymphocyte proportion in lymphoid organs (Table 2).

Table 2 shows peripheral lymphoid organ depletion induced by a single ATG injection. Peripheral lymphoid organs were sampled 14 days after onset of immunosuppressive treatment administration. Values presented are the percentages of CD4, CD8, CD49d and B220 cells observed in the spleen and maxillary lymph nodes, and the absolute values of CD4, CD8, CD49d and B220 by reference to the number of lymphocytes contained in each organ.

|       |            | Spleen           |      | Lymph nodes      |      |
|-------|------------|------------------|------|------------------|------|
|       |            | $10^6$ cells/ml  | %    | $10^6$ cells/ml  | %    |
| CD4+  | PBS        | 1.3              | 13.8 | 0.7              | 34.7 |
|       | NRS        | 0.8              | 14.2 | 0.4              | 35.2 |
|       | ATG        | 0.7              | 12.3 | 0.1              | 25   |
|       | Fludarabine| 3.8              | 20.4 | 0.3              | 31.3 |
| CD8+  | PBS        | 1                | 10.4 | 0.6              | 31   |
|       | NRS        | 0.5              | 10.1 | 0.3              | 32.6 |
|       | ATG        | 0.2              | 3.9  | 0.07             | 13.4 |
|       | Fludarabine| 2.5              | 13.4 | 0.3              | 35.3 |
| CD49d+| PBS        | 0.5              | 5.6  | 0.06             | 3.2  |
|       | NRS        | 0.3              | 5.6  | 0.03             | 3.6  |
|       | ATG        | 0.3              | 5.1  | 0.02             | 2.7  |
|       | Fludarabine| 1.4              | 7.5  | 0.03             | 3.8  |
| B220+ | PBS        | 6.7              | 69.4 | 0.6              | 31.9 |
|       | NRS        | 3.7              | 68.4 | 0.3              | 30   |
|       | ATG        | 3.7              | 64   | 0.3              | 56.4 |
|       | Fludarabine| 8                | 42.4 | 0.3              | 30.2 |

The percentage of T and NK cells was increased in spleen 6 days after the end of Fludarabine treatment. This was particularly obvious for CD4+ T cells and to a lesser extend for CD8+ and NK cells. In accordance, the percentage of B220+ cells was markedly decreased 6 days after the end of treatment. Upon ATG treatment, the percentages of T cells were decreased in spleen and lymph nodes resulting in a marked drop in CD4+ and CD8+ counts. CD8+ lymphocytes were more affected than CD4+ T cells. Of note, the total number of lymphocytes recovered in spleens from Fludarabine treated animals was markedly higher than that from controls. Also the percentage of null cells in spleens from ATG- and Fludarabine treated animals exceeded 15%. None of these were observed at the level of lymph nodes.

2.2.5 Increased Magnitude of CEA-Specific Th1 Response as a Result of Immunosuppression and Prime-Boost Immunization.

The Inventors next determined the impact of lymphodepletion performed in the conditions described above on the magnitude of CEA-specific T cell response in their immunization model. Seven days prior to prime-boost immunization, animals were treated with Fludarabine or ATG as described above. As compared to PBS control, the magnitude of CEA-specific cellular immune response was decreased in Fludarabine treated animals immunized with CyaA-CEA$_{A3B3}$ in presence of CpG adjuvant. Surprisingly, in the group of ATG treated animals, the magnitude of CEA-specific cellular immune response was doubled as compared to controls. CEA-specific cellular immune responses were also detected upon immunization with a non-relevant recombinant CyaA bearing the HPV16E7 antigen. Lower CEA-specific cellular immune responses were detected upon CpG-formulated His-tag CEA and CyaAΔ-CEA$_{A3B3}$ immunization thus highlighting the importance of CD11b targeting for the described effect to be maximal.

2.2.6 Increased Survival Median Following CyaA-CEA$_{A3B3}$ Prime Boost Immunization as a Result or Prior Lymphoablation.

The Inventors next tested the relevance of this observation in a tumor rejection model. They used MC38 murine colon adenocarcinoma cells stably expressing CEA protein (48). Upon injection of $5 \times 10^5$ tumor cells, mock-, CyaAΔ-CEA$_{A3B3}$ and His-Tag-CEA-treated animals developed tumors and became moribund, necessitating euthanasia (FIG. 10). In these conditions, the survival medians of the animals were 13-15 days respectively. In contrast, animals immunized 10 days after tumor injection, with CyaA-CEA$_{A3B3}$+CpG, had enhanced survival medians (27 days). Upon treatment with ATG, the survival median of mock-treated animals was enhanced to 19-21 days. In this group, 80% of CyaA-CEA$_{A3B3}$+CpG treated animals had complete tumor regression and were still alive at day 60. Animals treated with Fludarabine had a completely different pattern of tumor growth. MCa32A growth was partially inhibited by Fludarabine treatment lasting 6 days. As a consequence, the survival median of mock-treated animals was enhanced to 21-25 days. Sixty percent of CyaA-CEA$_{A3B3}$+CpG treated animals had complete tumor regression and were still alive at day 60.

2.3 Discussion

Many issues hamper the translation of pre-clinical results to the clinic in the field of cell-based adoptive tumor immunotherapy. One of them is the magnitude of the induced adoptive response to the tumor-associated antigen (TAA) of interest. Indeed, in humans the growth and efficacy of antigen specific T cells are limited by multiple factors in the context of tumor development. These include, lack of induction of T cell clones with high affinity to the TAA, negative signals from regulatory cells, tumor stroma and homeostatic T cell regulation. In murine models of adoptive T cell transfer therapies, lymphodepletion has been shown to increase engraftment and persistence of transferred cells (43-46). Such strategies have been quite successfully translated to the clinic most recently (36-38). Using a powerful tool for inducing specific CD8+ and CD4+ T cell responses, the adenylate cyclase from *B. pertussis*, the Inventors analyzed the impact of lymphodepletion on active immunization aimed at inducing specific T cell responses. They chose to target the Carcino-Embryonic Antigen because of its overexpression in numerous types of cancer.

The efficiency of CyaA as a vector tool has been shown to be unaffected by prior immunity (20, 21), thus allowing homologous prime-boost strategies. By using two different routes of injection, the Inventors were able to increase the importance of CEA-specific immune response. They were not able to further amplify the cellular immune response by a second id boost. They then analyzed the impact of lymphodepletion in the context of active immunisation mediated by CyaA and CpG adjuvant. The Inventors focused on products extensively used in humans that have been shown to preferentially deplete T lymphocytes. The overall level of lymphodepletion obtained with Fludarabine was inferior to that of ATG.

Prior Fludarabine-induced immunosuppression had a negative impact on the frequency of CEA-specific T lymphocytes upon prime boost vaccination with CyaA-CEA$_{A3B3}$+CpG adjuvant. Surprisingly, prior ATG-mediated lymphodepletion resulted in doubling the frequency of CEA-specific T lymphocytes upon prime boost vaccination with CyaA-CEA$_{A3B3}$+CpG adjuvant. Whether this is due to the disruption of homeostatic T cell regulation or the destruction of regulatory T cells remains to be investigated. The Inventors cannot exclude that lymphodepletion induces higher levels of cytokines to be available for remaining activated lymphocytes so as to facilitate their development and amplification. The described effect is quite remarkable and unexpected taking into account the level of lymphodepletion at the time of immunization as it is described in FIG. 8 and table 2. At the time of prime immunization, there were 20-13 times more circulating lymphocytes in the control groups than in the ATG group. At the time of boost immunization, there were 6 times more circulating lymphocytes in the control groups than in the ATG group. Lymphodepletion measured in lymphoid organs was about the same order of magnitude.

Lymphodepletion increased the frequency of CEA-specific CD8+ T cells to a less important level upon His-tag CEA+CpG and CyaAΔ-CEA$_{43B3}$+CpG immunization. This highlights the importance of APC targeting in the phenomenon described here. CyaA vector targets DC through its property to translocate its catalytic domain into the cytosol of CD11b+antigen presenting cells (17, 18). Of interest, the Inventors observed a similar result of increased frequency of CEA- specific CD8+lymphocytes following lymphodepletion with another system vectorization, the hsp65 protein of M. bovis fused to CEA$_{43B3}$ (data not shown). At the exception of Fludarabine-treated animals, the frequency of CEA-specific CD8+ T cells was linked to the ability of animals to survive to tumor challenge mediated by MCa32A cells indicating a correlation between the number of CEA-specific lymphocytes and the ability for the mice to control and/or reject CEA expressing tumor cells. Fludarabine is an antimetabolite and has delayed MCa32A tumor growth while it was given to the animals. Indeed, at the time of CyaA-based immunotherapy the size of tumors in Fludarabine group was 20 times smaller than in the other groups. It is probably why CyaA-CEA$_{43B3}$+CpG adjuvant immunotherapy was so efficient as compared to control group.

This study demonstrates that CyaA-based immunotherapy is compatible with lymphodepletion mediated by ATG. In such a context, prime-boost immunization by two different routes of injection (iv, id) markedly increased the frequency of CEA-specific CD8+ T cells. This increased frequency of CEA-specific cytotoxic T lymphocytes correlated with a better ability to control and/or reject CEA expressing tumor cells. From the results presented, it is mandatory to use a vector that targets antigen presenting cells such as CyaA or hsp65 to obtain such a result. Indeed, CyaAΔ which is devoid of CD11b binding has totally lost its ability to induce CEA-specific T cells. CyaA-based immunotherapy is also compatible with lymphodepletion mediated by Fludarabine resulting in increased survival to tumor challenge.

REFERENCES

1. Awwad, M. and North, R. J. Cyclophosphamide-induced immunologically mediated regression of -a cyclophosphamide-resistant murine tumor: a consequence of eliminating precursor L3T4+ suppressor T-cells. Cancer Res, 49: 1649-1654, 1989.
2. Berd, D., Maguire, H. C., Jr., and Mastrangelo, M. J. Induction of cell-mediated immunity to autologous melanoma cells and regression of metastases after treatment with a melanoma cell vaccine preceded by cyclophosphamide. Cancer Res, 46: 2572-2577, 1986.
3. Berd, D., Maguire, H. C., Jr., McCue, P., and Mastrangelo, M. J. Treatment of metastatic melanoma with an autologous tumor-cell vaccine: clinical and immunologic results in 64 patients. J Clin Oncol, 8: 1858-1867, 1990.
4. Berd, D., Murphy, G., Maguire, H. C., Jr., and Mastrangelo, M. J. Immunization with haptenized, autologous tumor cells induces inflammation of human melanoma metastases. Cancer Res, 51: 2731-2734, 1991.
5. Hengst, J. C., Mokyr, M. B., and Dray, S. Cooperation between cyclophosphamide tumoricidal activity and host antitumor immunity in the cure of mice bearing large MOPC-315 tumors. Cancer Res, 41: 2163-2167, 1981.
6. Reissmann, T., Voegeli, R., Pohl, J., and Hilgard, P. Augmentation of host antitumor immunity by low doses of cyclophosphamide and mafosfamide in two animal tumor models. Cancer Immunol Immunother, 28: 179-184, 1989.
7. Sahasrabudhe, D. M., deKernion, J. B., Pontes, J. E., Ryan, D. M., O'Donnell, R. W., Marquis, D. M., Mudholkar, G. S., and McCune, C. S. Specific immunotherapy with suppressor function inhibition for metastatic renal cell carcinoma. J Biol Response Mod, 5: 581-594, 1986.
8. Ben-Efraim, S., Bocian, R. C., Mokyr, M. B., and Dray, S. Increase in the effectiveness of melphalan therapy with progression of MOPC-315 plasmacytoma tumor growth. Cancer Immunol Immunother, 15: 101-107, 1983.
9. Nagarkatti, M., Toney, D. M., and Nagarkatti, P. S. Immunomodulation by various nitrosoureas and its effect on the survival of the murine host bearing a syngeneic tumor. Cancer Res, 49: 6587-6592, 1989.
10. North, R. J. and Awwad, M. Elimination of cycling CD4+ suppressor T cells with an anti-mitotic drug releases non-cycling CD8+ T cells to cause regression of an advanced lymphoma. Immunology, 71: 90-95, 1990.
11. Morikawa, K., Hosokawa, M., Hamada, J., Sugawara, M., and Kobayashi, H. Host-mediated therapeutic effects produced by appropriately timed administration of bleomycin on a rat fibrosarcoma. Cancer Res, 45: 1502-1506, 1985.
12. Chun, H. G., Leyland-Jones, B., and Cheson, B. D. Fludarabine phosphate: a synthetic purine antimetabolite with significant activity against lymphoid malignancies. J Clin Oncol, 9: 175-188, 1991.
13. Cheson, B. D. Infectious and immunosuppressive complications of purine analog therapy. J Clin Oncol, 13: 2431-2448, 1995.
14. Frank, D. A., Mahajan, S., and Ritz, J. Fludarabine-induced immunosuppression is associated with inhibition of STAT1 signaling. Nat Med, 5: 444-447, 1999.
15. Ladant, D. and Ullmann, A. *Bordetella pertussis* adenylate cyclase: a toxin with multiple talents. Trends Microbiol, 7: 172-176, 1999.
16. Morón, G., Dadaglio, G., and Leclerc, C. New tools for antigen delivery to the MHC class I pathway. Trends in Immunology, 25: 92-97, 2004.
17. Guermonprez, P., Khelef, N., Blouin, E., Rieu, P., Ricciardi-Castagnoli, P., Guiso, N., Ladant, D., and Leclerc, C. The adenylate cyclase toxin of *Bordetella pertussis* binds to target cells via the alpha(M)beta(2) integrin (CD11b/CD18). J Exp Med, 193: 1035-1044, 2001.
18. Guermonprez, P., Fayolle, C., Rojas, M. J., Rescigno, M., Ladant, D., and Leclerc, C. In vivo receptor-mediated delivery of a recombinant invasive bacterial toxoid to CD11c+CD8 alpha-CD11b high dendritic cells. Eur J Immunol, 32: 3071-3081, 2002.

19. Fayolle, C., Ladant, D., Karimova, G., Ullmann, A., and Leclerc, C. Therapy of murine tumors with recombinant *Bordetella pertussis* adenylate cyclase carrying a cytotoxic T cell epitope. J Immunol, 162: 4157-4162, 1999.

20. Fayolle, C., Osickova, A., Osicka, R., Henry, T., Rojas, M. J., Saron, M. F., Sebo, P., and Leclerc, C. Delivery of multiple epitopes by recombinant detoxified adenylate cyclase of *Bordetella pertussis* induces protective antiviral immunity. J Virol, 75: 7330-7338, 2001.

21. Preville, X., Ladant, D., Timmerman, B., and Leclerc, C. Eradication of established tumors by vaccination with recombinant *Bordetella pertussis* adenylate cyclase carrying the human papillomavirus 16 E7 oncoprotein. Cancer Res, 65: 641-649, 2005.

22. Rosenberg, S. A., Yang, J. C., and Restifo, N. P. Cancer immunotherapy: moving beyond current vaccines. Nat Med, 10: 909-915, 2004.

23. Starzl, T. E., Marchioro, T. L., Hutchinson, D. E., Porter, K. A., Cerilli, G. J., and Brettschneider, L. The clinical use of antilymphocyte globulin in renal homotransplantation. Transplantation, 5: Suppl1:1100-1105, 1967.

24. Storb, R., Gluckman, E., Thomas, E. D., Buckner, C. D., Clift, R. A., Fefer, A., Glucksberg, H., Graham, T. C., Johnson, F. L., Lerner, K. G., Neiman, P. E., and Ochs, H. Treatment of established human graft-versus-host disease by antithymocyte globulin. Blood, 44: 56-75, 1974.

25. Marsh, J., Schrezenmeier, H., Marin, P., Ilhan, O., Ljungman, P., McCann, S., Socie, G., Tichelli, A., Passweg, J., Hows, J., Raghavachar, A., Locasciulli, A., and Bacigalupo, A. Prospective randomized multicenter study comparing cyclosporin alone versus the combination of antithymocyte globulin and cyclosporin for treatment of patients with nonsevere a plastic anemia: a report from the European Blood and Marrow Transplant (EBMT) Severe A plastic Anaemia Working Party. Blood, 93: 2191-2195, 1999.

26. Ringden, O., Remberger, M., Carlens, S., Hagglund, H., Mattsson, J., Aschan, J., Lonnqvist, B., Klaesson, S., Winiarski, J., Dalianis, T., Olerup, O., Sparrelid, E., Elmhom-Rosenborg, A., Svahn, B. M., and Ljungman, P. Low incidence of acute graft-versus-host disease, using unrelated HLA-A-, HLA-B-, and HLA-DR-compatible donors and conditioning, including anti-T-cell antibodies. Transplantation, 66: 620-625, 1998.

27. Aversa, F., Tabilio, A., Velardi, A., Cunningham, I., Terenzi, A., Falzetti, F., Ruggeri, L., Barbabietola, G., Aristei, C., Latini, P., Reisner, Y., and Martelli, M. F. Treatment of high-risk acute leukemia with T-cell-depleted stem cells from related donors with one fully mismatched HLA haplotype. N Engl J Med, 339: 1186-1193, 1998.

28. Preville, X., Flacher, M., LeMauff, B., Beauchard, S., Davelu, P., Tiollier, J., and Revillard, J. P. Mechanisms involved in antithymocyte globulin immuno suppressive activity in a nonhuman primate model. Transplantation, 71: 460-468, 2001.

29. Preville, X., Nicolas, L., Flacher, M., and Revillard, J. P. A quantitative flow cytometry assay for the preclinical testing and pharmacological monitoring of rabbit antilymphocyte globulins (rATG). Journal of Immunological Methods, 245: 45-54, 2000.

30. Gmira, S., Karimova, G., and Ladant, D. Characterization of recombinant *Bordetella pertussis* adenylate cyclase toxins carrying passenger proteins. Res Microbiol, 152: 889-900, 2001.

31. El-Azami-El-Idrissi, M., Bauche, C., Loucka, J., Osicka, R., Sebo, P., Ladant, D., and Leclerc, C. Interaction of *Bordetella pertussis* adenylate cyclase with CD11b/CD18: Role of toxin acylation and identification of the main integrin interaction domain. J Biol Chem, 278: 38514-38521, 2003.

32. Ullenhag, G. J., Fagerberg, J., Strigard, K., Frodin, J. E., and Mellstedt, H. Functional HLA-DR T cell epitopes of CEA identified in patients with colorectal carcinoma immunized with the recombinant protein CEA. Cancer Immunol Immunother, 53: 331-337, 2004.

33. Greiner, J. W., Zeytin, H., Anver, M. R., and Schlom, J. Vaccine-based therapy directed against carcinoembryonic antigen demonstrates antitumor activity on spontaneous intestinal tumors in the absence of autoimmunity. Cancer Res, 62: 6944-6951, 2002.

34. Mennuni, C., Calvaruso, F., Facciabene, A., Aurisicchio, L., Storto, M., Scarselli, E., Ciliberto, G., and La Monica, N. Efficient induction of T-cell responses to carcinoembryonic antigen by a heterologous prime-boost regimen using DNA and adenovirus vectors carrying a codon usage optimized cDNA. Int J Cancer, 117: 444-455, 2005.

35. El Azami El Idrissi, M., Ladant, D., and Leclerc, C. The adenylate cyclase of *Bordetella pertussis*: a vector to target antigen presenting cells. Toxicon, 40: 1661-1665, 2002.

36. Dudley, M. E., Wunderlich, J. R., Robbins, P. F., Yang, J. C., Hwu, P., Schwartzentruber, D. J., Topalian, S. L., Sherry, R., Restifo, N. P., Hubicki, A. M., Robinson, M. R., Raffeld, M., Duray, P., Seipp, C. A., Rogers-Freezer, L., Morton, K. E., Mavroukakis, S. A., White, D. E., and Rosenberg, S. A. Cancer regression and autoimmunity in patients after clonal repopulation with antitumor lymphocytes. Science, 298: 850-854, 2002.

37. Dudley, M. E., Wunderlich, J. R., Yang, J. C., Sherry, R. M., Topalian, S. L., Restifo, N. P., Royal, R. E., Kammula, U., White, D. E., Mavroukakis, S. A., Rogers, L. J., Gracia, G. J., Jones, S. A., Mangiameli, D. P., Pelletier, M. M., Gea-Banacloche, J., Robinson, M. R., Berman, D. M., Filie, A. C., Abati, A., and Rosenberg, S. A. Adoptive cell transfer therapy following non-myeloablative but lymphodepleting chemotherapy for the treatment of patients with refractory metastatic melanoma. J Clin Oncol, 23: 2346-2357, 2005.

38. Gattinoni, L., Powell, D. J., Jr., Rosenberg, S. A., and Restifo, N. P. Adoptive immunotherapy for cancer: building on success. Nat Rev Immunol, 6: 383-393, 2006.

39. Keating, M. J., Kantarjian, H., Talpaz, M., Redman, J., Koller, C., Barlogie, B., Velasquez, W., Plunkett, W., Freireich, E. J., and McCredie, K. B. Fludarabine: a new agent with major activity against chronic lymphocytic leukemia. Blood, 74: 19-25, 1989.

40. Boldt, D. H., Von Hoff, D. D., Kuhn, J. G., and Hersh, M. Effects on human peripheral lymphocytes of in vivo administration of 9-beta-D-arabinofuranosyl-2-fluoroadenine-5'-monophosphate (NSC 312887), a new purine antimetabolite. Cancer Res, 44: 4661-4666, 1984.

41. Kuwatani, M., Ikarashi, Y., Mineishi, S., Asaka, M., and Wakasugi, H. An irradiation-free nonmyeloablative bone marrow transplantation model: importance of the balance between donor T-cell number and the intensity of conditioning. Transplantation, 80: 1145-1152, 2005.

42. Petrus, M. J., Williams, J. F., Eckhaus, M. A., Gress, R. E., and Fowler, D. H. An immunoablative regimen of fludarabine and cyclophosphamide prevents fully MHC-mismatched murine marrow graft rejection independent of GVHD. Biol Blood Marrow Transplant, 6: 182-189, 2000.

43. Berenson, J. R., Einstein, A. B., Jr., and Fefer, A. Syngeneic adoptive immunotherapy and chemoimmunotherapy of a Friend leukemia: requirement for T cells. J Immunol, 115: 234-238, 1975.

44. Eberlein, T. J., Rosenstein, M., and Rosenberg, S. A. Regression of a disseminated syngeneic solid tumor by systemic transfer of lymphoid cells expanded in interleukin 2. J Exp Med, 156: 385-397, 1982.

45. North, R. J. Cyclophosphamide-facilitated adoptive immunotherapy of an established tumor depends on elimination of tumor-induced suppressor T cells. J Exp Med, 155: 1063-1074, 1982.

46. Rosenberg, S. A., Spiess, P., and Lafreniere, R. A new approach to the adoptive immunotherapy of cancer with tumor-infiltrating lymphocytes. Science, 233: 1318-1321, 1986.

47. Badovinac, V. P., Messingham, K. A., Jabbari, A., Hating, J. S., and Harty, J. T. Accelerated CD8+ T-cell memory and prime-boost response after dendritic-cell vaccination. Nat Med, 11: 748-756, 2005.

48. Robbins, P. F., Kantor, J. A., Salgaller, M., Hand, P. H., Fernsten, P. D., and Schlom, J. Transduction and Expression of the Human Carcinoembryonic Antigen Gene in a Murine Colon Carcinoma Cell Line. Cancer Res, 51: 3657-3662, 1991.

The invention claimed is:

1. A kit comprising:
   a first composition comprising a first compound provoking lymphocytopenia, wherein the first compound is an anti-thymocyte immunoglobulin (ATG) present in an amount capable of provoking transient T cell depletion;
   a second composition comprising a second compound having selective affinity for professional antigen presenting cells (APC), wherein said second compound is covalently coupled to a T cell epitope of an antigen from cellular malignancy, dysplasia, tumour or cancer, and wherein said second compound is selected from the group consisting of adenylate cyclases (CyaA), heat shock proteins (HSP), shigatoxin and LAG-3; and wherein the antigen from cellular malignancy, dysplasia, tumour or cancer is selected from the group consisting of carcino-embryonic antigen (CEA), MAGE -A3, telomerase (TERT), E7 oncogene from the human papilloma virus (HPV) and P53;
   for sequential use in the treatment and/or prevention of cellular malignancy, dysplasia, tumour or cancer in a patient.

2. The kit according to claim 1, wherein the adenylate cyclase is from *Bordetella pertussis*, the HSP is selected from the group consisting of hsp65 and hsp70, and said shigatoxin is from *Shigella dysenteriae*.

3. The kit according to claim 1, wherein said second compound and said at least one T cell epitope are polypeptides encoded by DNA sequences fused by recombinant DNA technology.

4. The kit according to claim 1, wherein the patient is a human.

5. The kit according to claim 1, wherein said first and second compositions are formulated for intramuscular, intravenous, intradermal, cutaneous, subcutaneous, intraperitoneal, mucosal or oral administration.

6. The kit according to claim 2, wherein said hsp65 and hsp70 are from *Mycobacterium bovis*.

* * * * *